(12) United States Patent
Panthier et al.

(10) Patent No.: US 9,201,076 B2
(45) Date of Patent: *Dec. 1, 2015

(54) UPREGULATION OF RACK-1 IN MELANOMA AND ITS USE AS A MARKER

(71) Applicants: Institut Pasteur, Paris (FR); Centre National de la Recherche Scientifique, Paris (FR); Institut Curie, Paris (FR); Ecole Nationale Veterinaire D'Alfort, Maisons Alfort (FR); Institut National de la Recherche Agronomique (INRA), Paris (FR)

(72) Inventors: Jean-Jacques Panthier, Paris (FR); Giorgia Egidy, Paris (FR); Xavier Sastre-Garau, Vincennes (FR); Florence Bernex, Paris (FR)

(73) Assignees: Institut Pasteur, Paris (FR); Ecole Nationale Veterinaire D'Alfort, Maisons Alfort (FR); Institut Curie, Paris (FR); Centre National de la Recherche Scientifique, Paris (FR); Institut National de la Recherche Agronomique (INRA), Paris (FR)

( * ) Notice: Subject to any disclaimer, the term of this patent is extended or adjusted under 35 U.S.C. 154(b) by 101 days.

This patent is subject to a terminal disclaimer.

(21) Appl. No.: 13/730,243

(22) Filed: Dec. 28, 2012

(65) Prior Publication Data

US 2013/0273532 A1   Oct. 17, 2013

Related U.S. Application Data

(60) Division of application No. 12/671,415, filed as application No. PCT/EP2008/006189 on Jul. 28, 2008, now Pat. No. 8,367,348, which is a continuation-in-part of application No. 11/831,128, filed on Jul. 31, 2007, now abandoned.

(51) Int. Cl.
*C12Q 1/68* (2006.01)
*G01N 33/68* (2006.01)
*G01N 33/574* (2006.01)

(52) U.S. Cl.
CPC .......... *G01N 33/6893* (2013.01); *C12Q 1/6886* (2013.01); *G01N 33/5743* (2013.01); *C12Q 2600/112* (2013.01); *C12Q 2600/158* (2013.01); *G01N 2333/705* (2013.01); *G01N 2333/9121* (2013.01)

(58) Field of Classification Search
None
See application file for complete search history.

(56) References Cited

U.S. PATENT DOCUMENTS

| 8,247,182 | B2 | 8/2012 | Panthier et al. | |
| 8,367,348 | B2 * | 2/2013 | Panthier et al. | 435/7.1 |
| 2010/0297632 | A1 | 11/2010 | Panthier et al. | |

FOREIGN PATENT DOCUMENTS

WO   2005/054508 A   6/2005

OTHER PUBLICATIONS

Talantov et al (Clin Cancer Res, 2005, 11(20): 7234-7242).*
Berrington et al (Vet Pathol, 1994, 31: 455-461).*
Ramos-Vara et al (Vet Pathol, 2000, 37: 597-608).*
Ehlers et al (Clin Cancer Res, 2005, 11(5): Abstract).*
Jungbluth et al (Am J Surg Path, 1998, 22(5): Abstract).*
Buton-Wurster et al (J Hered, 2005, 96(7): Abstract).*
Murphy et al (Vet Pathol, 1979, 16(5): Abstract).*
Fleury et al (Pigment Cell Res, 2000, 13(1): Abstract).*
Edigy, G., et al., Molecular Cancer, vol. 7, p. 34 (2008).
Lopez-Bergami, et al., Mol. Cell, vol. 19, pp. 309-320 (2005).
Park, et al., JCS, vol. 117, pp. 3659-3668 (2004).
Office Action mailed Nov. 4, 2011, in U.S. Appl. No. 12/830,775.
Saito, A et al., Journal of Clinical Pathology, vol. 55, pp. 34-39 (2002).
Tadokoro, Taketsugu et al., Journal of Investigation Dermatology, vol. 124, No. 6, pp. 1326-1332 (2005).
Tockman et al., Cancer Res., vol. 52, pp. 2711s-2718s (1992).

* cited by examiner

*Primary Examiner* — Sean Aeder
(74) *Attorney, Agent, or Firm* — Law Office of Salvatore Arrigo and Scott Lee, LLP

(57) ABSTRACT

The present invention concerns a method for diagnosing a melanoma in a mammal comprising the detection of the overexpression of RACK-1 protein in a melanocyte cell of said mammal, and the deduction of the presence of a melanoma from the overexpression of RACK-1 protein. The invention is also directed to a method for determining the tumoral status of a melanocyte cell of a mammal, comprising the detection of overexpression of RACK-1 protein in the melanocyte cell, and the deduction of the tumoral state of said cell from the overexpression of RACK-1 protein.

18 Claims, 26 Drawing Sheets

UPREGULATION OF RACK-1 IN MELANOMA AND ITS USE AS A MARKER

This application is a divisional of application Ser. No. 12/671,415 (now U.S. Pat. No. 8,367,348 B2, issued Feb. 5, 2013), which is the national stage of International Application No. PCT/EP2008/006189, filed Jul. 28, 2008, which is a continuation-in-part of application Ser. No. 11/831,128, filed Jul. 31, 2007 (abandoned). All of these applications are hereby incorporated herein by reference.

Throughout this specification and experimental part, reference is made to different publications. These publications are hereby incorporated by reference.

FIELD OF THE INVENTION

The present invention is in the domain of cancer; it relates to a method for diagnosing a cancer in a mammal.

BACKGROUND OF THE INVENTION

Melanoma is a malignant tumor developing by transformation of melanocytes, the cells which produce the pigment melanin that colors skin, hair, and eyes and is heavily concentrated in most moles. The majority of melanomas, therefore, are black or brown. However, melanomas occasionally stop producing pigment. When that happens, the melanomas may no longer be dark, but are skin-colored, pink, red or purple.

Melanoma is the most serious form of skin cancer. Its incidence and mortality rates in fair-skinned populations increase worldwide. While it is not the most common of the skin cancers, it causes the most deaths. The American Cancer Society estimates that in 2007, there will be around 60 000 new cases of melanoma in the United States.

Everyone is susceptible to develop a melanoma, but depending on several factors, the risk can be increased, *inter alia* sun exposure, number of moles on the skin, skin type and genetic background. Indeed, both UVA and UVB rays can induce skin cancer, including melanoma. The presence of the two types of moles, normal moles and atypical moles, known as dysplastic naevi, are indicative of an increased risk of melanoma. Regarding the genetic predisposition, it is known that about 10% of the patients diagnosed with melanoma have a family member with a history of melanoma.

Primary melanomas are likely to produce metastases, indicative of the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body.

Presence of metastases carries a severe prognosis due to ineffective response to treatments.

Regarding diagnosis, moles that are irregular in color or shape are suspicious of a malignant or a premalignant melanoma. Following a visual examination and a dermatologic exam, a biopsy of the suspicious mole may also be made. If it is malignant, the mole and an area around it need excision to avoid expansion and spread.

Clinical and histopathological criteria are useful as indicators for patients presenting primary melanoma. However it is widely admitted that precise diagnostic and prognostic markers would be beneficial for a number of patients.

Early and reliable diagnosis of a melanoma is thus of outmost importance.

Melanomas are also frequently observed on horses, where they are the most common skin tumors in adult horses. Melanomas have been shown to occur more commonly in Arabian, Lipizzaner, and Percheron breeds, as these breeds have a high incidence of gray horses and melanomas are mostly found in gray horses. These melanomas are generally found around the lips, eyes, ears, salivary glands, anus, penis, and vulva. Most melanomas in gray horses are benign slow-growing tumors that rarely metastasize or spread to other organs. However, the tumor can spread to other organs, especially in non-gray horses. Generally, these tumors do not cause a problem other than with urination, defecation, or breeding. However, they can invade local tissue and can cause lameness as well as neurological problems by invading the central nervous system.

Melanomas can also be observed on dogs. Although found primarily on the skin, in the dog, they can also be found in the oral cavity. Early diagnosis of melanomas can lead to more successful attempts at removal and identification of the grade or stage of cancer. Even the benign forms of cutaneous tumors can be locally invasive. Melanomas can metastasize (spread) to any area of the body especially the lymph nodes and lungs and present very challenging and dangerous prospects for the dog. Cats are also susceptible to melanoma tumors, however in a lesser extent than dogs.

Diagnosis of melanoma is thus also problematic from a veterinary point of view.

The diagnosis of melanoma requires experience, as early stages may look identical to harmless moles or not have any color at all.

If a melanoma is recognized and treated early, it is nearly 100 percent curable. But if it is not, the cancer can advance and spread to other parts of the body, where it becomes hard to treat and can be fatal.

There is thus a need for new tools allowing early and reliable diagnosis of melanoma.

Moreover, understanding the molecular bases of melanoma progression could help developing more effective treatments. Mechanisms of melanocyte transformation are thus widely studied.

SUMMARY OF THE INVENTION

The present invention concerns methods for determining the tumoral status of a melanocyte mammalian cell and for diagnosing a melanoma in a mammal. According to a first aspect of the invention, the method comprises the step of detecting overexpression of RACK-1 protein in a melanocyte mammalian cell and concluding that the cell is tumoral in case of overexpression, thus that the mammal presents a melanoma.

According to a second aspect of the invention, the method comprises determining the level of expression of RACK-1 protein in the melanocyte cell and comparing this level with a reference level. When the level of RACK-1 protein expression is increased in said melanocyte cell with respect to the reference level, it is to be concluded that the cell is a tumoral one and thus that the mammal presents a melanoma. Preferably, the reference level is the level of expression of RACK-1 protein in a normal, non-tumoral, melanocyte, i.e. a normal epidermal (cutaneous) melanocyte or a normal choroidal melanocyte.

The level of RACK-1 protein expression can be defined as the level of RACK-1 mRNA or protein.

The invention also relates to a method for diagnosing a melanoma in a mammal comprising the step of bringing a biological sample from said mammal into contact in vitro, with a means for detecting melanocyte cells and a means for detecting RACK-1 protein expression and the step of determining whether melanocyte cells co-localise with RACK-1 protein expression, presence of melanocyte cells exhibiting RACK-1 protein expression being indicative of a melanoma.

The sample may be advantageously a biopsy, for example a biopsy of lymph node, liver, lung, heart, spleen, eye or skin.

According to a preferred embodiment of the present invention, the mammal is a human. Alternatively, the mammal may be a pig, a cat, a dog or a horse.

In order to detect RACK-1 protein, especially by in situ immunoassay, antibodies against RACK-1 are preferably used.

The invention is also directed to a kit for diagnosing a melanoma in a mammal comprising a means for detecting RACK-1 protein expression. Such a kit advantageously further comprises a means for detecting melanocytic cells.

The invention concerns also the use of RACK-1 protein as a marker of tumoral melanocytes.

BRIEF DESCRIPTION OF THE DRAWINGS

The invention may be further illustrated by reference to the accompanying drawings wherein:

FIG. 1A is macrophotography of a lung infiltrated with multifocal, variably sized black melanoma metastases. Arrows point to some black spots of neoplastic tissue.

FIG. 1B2-D2: absence of non-specific staining without the primary antibody.

FIG. 1B1 and FIG. 1B2 correspond to normal skin, FIG. 1C1 and FIG. 1C2 correspond to cutaneous melanoma and FIG. 1D1 and FIG. 1D2 correspond to melanoma metastasis in a lung.

a stands for alveolae, be for bronchiolar epithelium, d for dermis, e for epidermis, hf for hair follicle. Arrows point to melanocytes (black) and melanoma cells (white). Scale bar for all micrographs is 100 µm.

FIGS. 2A to 2D depict the expression of RACK1 mRNA in pig tissues. In situ hybridisation autoradiography of RACK1 antisense (A) and sense (B) probes on depigmented sections. For each probe, normal (N) tissues are displayed on the left (skin, lung, liver and lymph node) and tumoral (T) tissues on the right (cutaneous melanoma, metastatic melanoma from lung, liver and lymph node). Note the intense signal on the tumors compared to the healthy or non-compromised tissues, with the antisense probe, except for lymph node. C: darkfield photomicrograph taken from a MeLiM melanoma lung metastasis hybridised with the antisense RACK1 probe. D: hematoxilin-eosin staining in a consecutive section from C with the pigmented area of the tumor which contains the silver grains on C. Scale bars in A, B: 1 cm, C, D: 100 µm.

FIGS. 3A to 3D depict RACK1 expression in normal pig epidermis. A, C, D: Confocal microscopy analysis of RACK1 protein (green), and double labelling for MITF (A, C) or DCT (D) (red) on pig skin. Normal epidermis from control Meishan minipig (A, B), and MeLiM (C, D). B is the transmission photograph corresponding to A. C: three dimensional 'orthogonal' slice projection analysis is included: the large central panel shows a single optical slice through which an x axis (green line) and a y axis (red line) were defined for sliced z-axis reconstruction. The corresponding results for the x, z slice (top) and the y, z slice (right) are shown. The blue line represents the position of the central panel image in the z stack. Nuclei are shown in blue. Note the RACK1 cytosolic spotty signal on keratinocytes and its absence in the melanocyte indicated by the white dashed line. Dotted lines show separation between dermis (d) and epidermis (e). Scale bars: 5 µm.

Figure 1A:
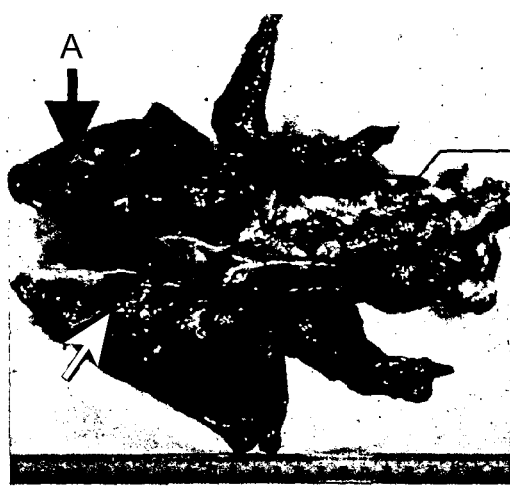
FIGS. 1A to 1D2 depict melanoma pulmonary metastases from MeLiM.
Figures 1, 1B:
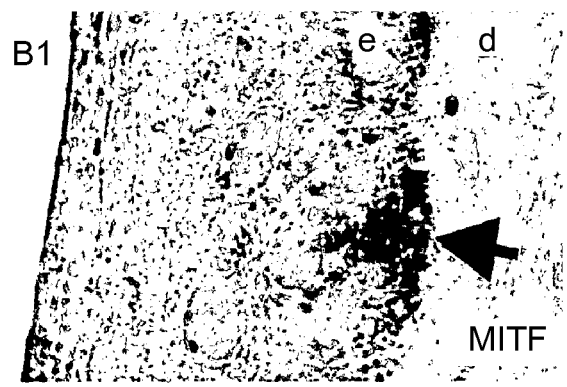
Figures 1, 4A:
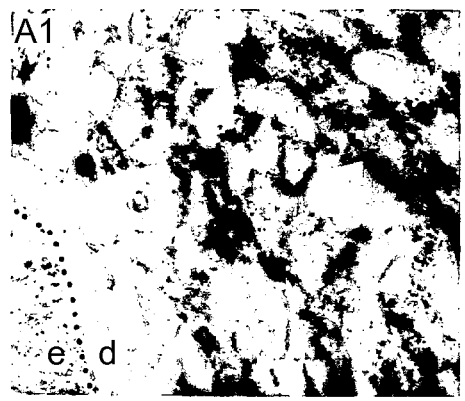
Figures 2, 4A:
Figures 3, 4A:
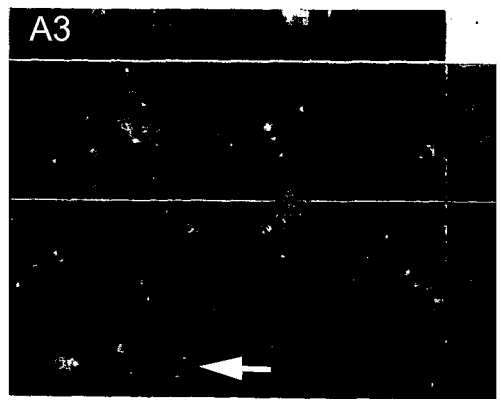
Figure 4B:
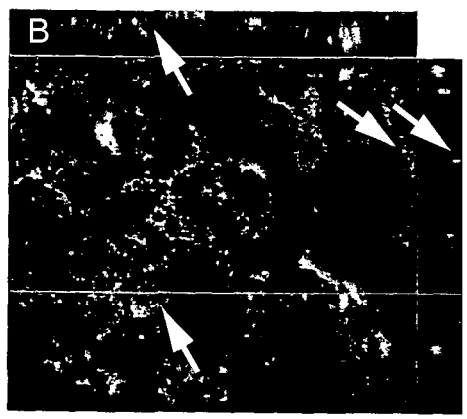
Figure 4C:
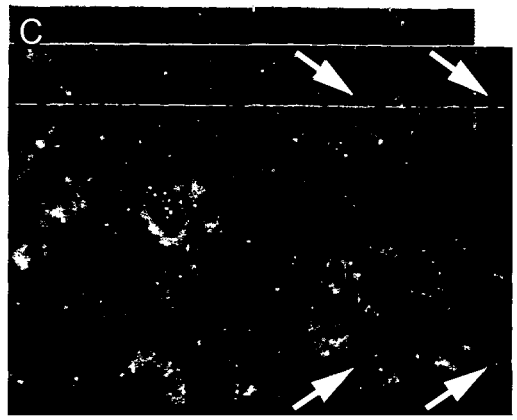
Figure 4D:
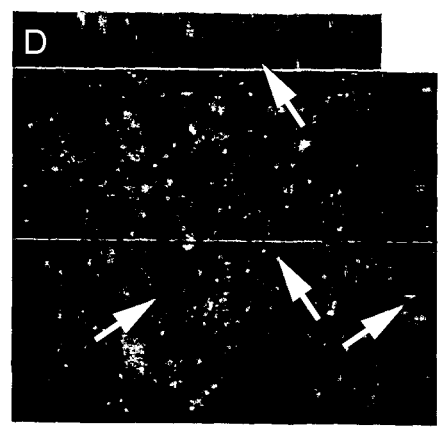

FIGS. 4A-1 to 4D illustrate the cellular distribution of RACK1 in MeLiM melanoma at different progression stages.

Confocal microscopy analysis of RACK1 protein (green), and double labelling for MITF (red). A: cutaneous melanoma. B-D: melanoma metastasis in a lymph node (B), lung (C) and heart (D). Three dimensional 'orthogonal' slice projection analysis is presented as in FIG. 3. Nuclei are shown in blue. A1: transmission photograph corresponding to A2. A3: zoom on the A2 inset. A: white arrowhead points at a dermal cutaneous melanoma cell positive for MITF and analysed by orthogonal projection. Note the comparable RACK1 cytosolic signal on dermal melanoma cells and epidermal keratinocytes. RACK1 is abundant in cutaneous and metastatic melanoma cells with perinuclear localization. Furthermore, in metastases, nuclear RACK1 is present, shown with yellow arrowheads on the optical slice and the orthogonal projections. Dotted lines in A1 and 2 show separation between dermis (d) and epidermis (e). Scale bars: 5 µm.

FIGS. 5A-1 to 5D-2 show the cellular distribution of β-catenin and RHEB in normal melanocytes and melanoma cells from MeLiM. Confocal microscopy and its respective transmission image on normal skin (A1-2, C1-2) and melanoma metastases in lung (B1-2, D1-2) after double labelling of RACK1 (red) and β-catenin (A, B) or RHEB (C, D) (green) are shown. Nuclear counterstaining is in blue. Arrows point at normal melanocytes with: cytosolic β-catenin (A1), perinuclear RHEB (C1), no RACK1. Arrowheads point at melanoma cells with nuclear signal for RACK1 and β-catenin in yellow (B1) or RHEB (D1) in white. Asterisk in A1 shows a keratinocyte with nuclear β-catenin, this is probably a dividing cell. Dotted lines in A, C show separation between dermis (d) and epidermis (e). Scale bars: 5 µm.

FIGS. 6A to 6F show RACK1 in human skin and melanoma. Confocal microscopy analysis of RACK1 protein (A, B), with double labelling for MITF (C, D) and nuclear counterstaining with Topro 3 (E, F). On the first column (A, C, E): control human skin. The MITF-positive melanocyte is surrounded by a dashed line. Dotted line shows separation between epidermis (e)-dermis (d) boundaries of the sample. On the second column (B, D, F): melanoma metastasis in lymph node. High levels of RACK1 are seen in the cytoplasm of metastasic human melanocytes. Scale bars: 10 µm.

FIGS. 7A to 7D show the high levels of RACK1 in human melanoma but not in nevi. Confocal microscopy of RACK1 (first raw) and MITF (second raw) on normal skin (a), nevus (b), cutaneous melanoma (c) and liver metastasis (d). Single optical sections taken with an SP2 Leica confocal microscope.

RACK1 is almost not detected in normal melanocytes (a). This also holds true in hyperproliferative lesions of nevi (b).

Sections of skin are from different patients. Arrowheads point to melanocytes where RACK1 is not detected. Arrows indicate melanocytes expressing cytoplasmic RACK1. Dotted line indicates epidermis-dermis boundary, e, epidermis; dr, dermis. Bar=10 µm.

Figure 8A:
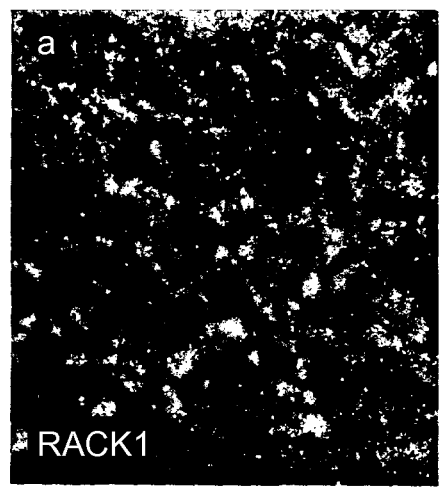
Figure 8B:
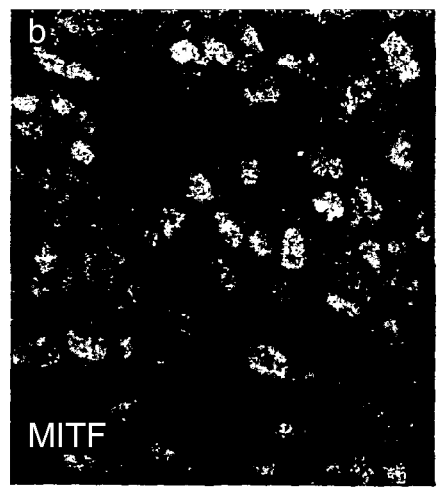
Figure 8C:
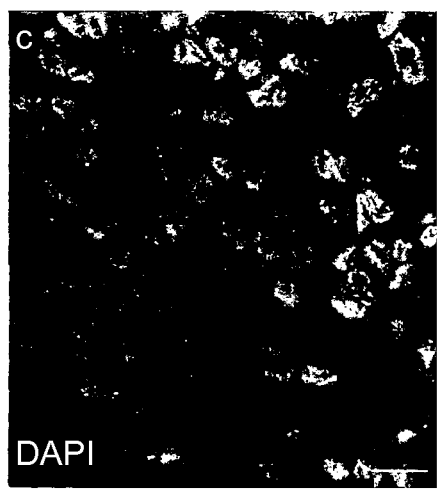

FIGS. 8A to 8C show the overexpression of RACK1 in uveal melanoma.

This Figure shows the high levels of RACK1 in human choroidal melanoma with chromosome 3 monosomy. Immunofluorescence staining of RACK1 (a) and MITF (b). In c, DAPI nuclear counterstaining Single optical section taken with an SPE Leica confocal microscope. Bar: 10 µm.

Figure 9A:
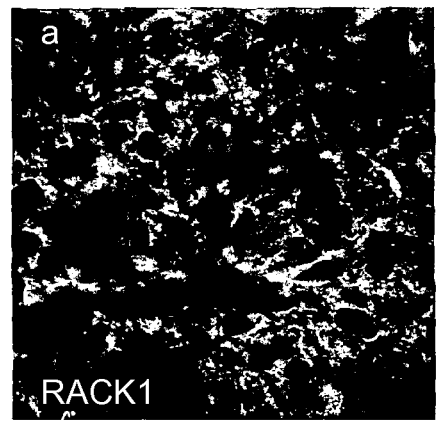
Figure 9B:
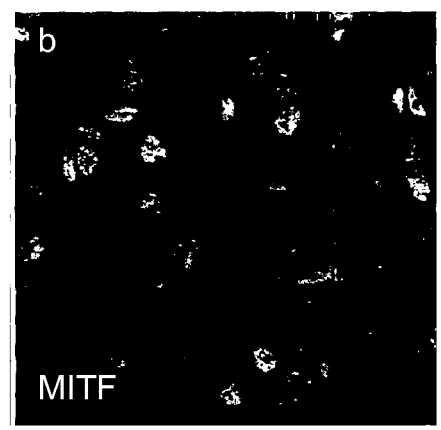
Figure 9C:
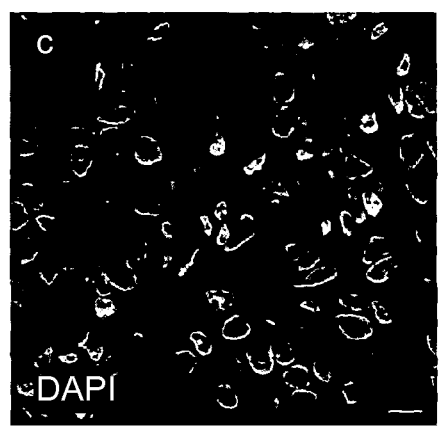

FIGS. 9A to 9C illustrate the overexpression of RACK1 in horse melanoma. High levels of RACK1 in horse cutaneous malignant melanoma. Immunofluorescence staining on RACK1 (a) and MITF (b). In c, DAPI nuclear counterstaining Single optical section taken with an Apo Tome Zeiss microscope. Bar: 10 µm.

The drawings in color are available at the European Patent Office as PCT Receiving Office for this application.

DETAILED DESCRIPTION OF EMBODIMENTS OF THE INVENTION

In the context of the present invention, the following terms are defined in the following manner:

Melanoma is a malignant tumor of melanocytes. Primarily it is a skin tumor (cutaneous melanoma), but it is also seen, though less frequently, for example in the melanocytes of the eye in humans (choroidal melanoma).

Metastasis is the spread of cancer from its primary site to other places in the body. Cancer cells can break off from a primary (or original) tumor, penetrate into lymphatic and blood vessels, circulate through the bloodstream, deposit and grow in a distant focus (metastasize) in other organs elsewhere in the body.

Tumors are classified as either benign or malignant. Malignant tumors can spread by invasion and metastasis while benign tumors cannot (and only grow locally). By definition, the term "cancer" applies only to malignant tumors.

Metastatic tumors are very common in the late stages of cancer. The spread of metastases may occur via the blood or the lymphatics or through both routes. The most common places for the metastases are the lymph nodes, liver, brain and the bones.

When cancer cells spread to form a new tumor, it is called a secondary, or metastatic tumor, and its cells are like those in the original tumor. This means that if melanoma spreads (metastasizes) to the lung, the secondary tumor (metastasis) is made up of tumoral melanocyte cells (not tumoral lung cells). The disease in the lung is metastatic melanoma.

The tumoral status of a cell is relevant to its tumoral or non-tumoral state, a tumoral cell meaning a cell which is not a normal, healthy one, but from a tumor. A tumoral cell may be from a benign or a malignant tumor.

RACK-1 (or RACK1) protein means the human protein encoded by the nucleotide sequence having the accession number NM_006098 in GeneBank (human protein P63244 SEQ ID N° 69) or an allelic variant, or any ortholog in another mammalian species, for example the murine sequence encoded by NM_008143 or the sequence of pig RACK-1 encoded by NM_214332, or the bovine sequence encoded by NM_175602 or the rat sequence encoded by NM_130734 or the canine sequence encoded by XM 537934. The RNA or DNA corresponding to RACK-1 protein can be detected with the following tag: ATTGTAGATG (SEQ ID No. 1).

The present invention relies on the finding by the inventors that the protein RACK-1 is overexpressed in tumoral melanocyte cells with respect to normal melanocyte cells of mammals. Indeed, in normal melanocytes, RACK-1 is expressed at a very low level and can hardly be detected. However, this protein has been found largely overexpressed in tumoral melanocyte cells, in a melanoma or in metastases of melanoma.

Moreover, the inventors have shown that, whereas the expression of RACK1 is highly increased and homogenously distributed in cutaneous and choroidal melanoma, the RACK1 signal is low and heterogeneous in nevi, i.e. in cutaneous benign tumors.

The invention also relies on the finding by the inventors, that RACK1 is overexpressed in all cutaneous and choroidal melanoma, according to their observations, contrary to other known markers which are only relevant for some but not all melanoma.

These data of the present inventors thus show that RACK1 is a universal marker of malignant tumors in melanocytes.

Therefore, according to a first embodiment, the present invention is directed to a method for determining the tumoral status of a melanocytic cell of a mammal, comprising the steps of detecting expression or overexpression of RACK-1 protein in the melanocyte cell and relating the expression or overexpression of RACK-1 protein to a tumoral state for said cell, preferably to a malignant tumoral state.

The tumoral status of the melanocytic cell under examination is preferably not determined before carrying out the method of the invention. The melanocytic cell is preferably not from an established cell-line. Preferably, the cell under examination is a primary cell.

The method of the invention thus allows detection of tumoral cells amongst melanocytic cells, preferably detection of malignant tumoral cells.

According to a second embodiment, the invention is also directed to a method for diagnosing a melanoma in a mammal comprising the steps of detecting expression or overexpression of RACK1 protein in a melanocytic cell of said mammal and relating the expression or overexpression of RACK-1 protein to the presence of a melanoma.

The methods are preferably carried out in vitro or ex vivo, that is the step of detection of expression or overexpression of RACK-1 protein is preferably carried out in vitro or ex vivo. Alternatively, it may be carried out in vivo.

A melanocytic cell can be recognised by its capacity to synthesize melanin. Thus any protein involved in the melanin synthesis may be used as a marker distinguishing melanocytic cells from other cells. It is however to be noted that some tumoral melanocytes may loose their capacity to produce melanin, another markers not involved in the melanin synthesis pathway may be used in that case. Potential markers for melanocytic cells are the microphthalmia transcription factor MITF, the dopachrome tautomerase DCT, the tyrosinase TYR and the tyrosinase-related protein 1 TRP1.

By overexpression of RACK1 protein, it is meant an expression which is above the expression of RACK-1 in a normal melanocytic cell used as control. According to the invention, RACK-1 over-expression can be detected on small amounts of primary tissue, paraffin embedded for example, which is available and used for pathologic diagnosis.

Moreover, according to these embodiments of the invention, the sole detection of the presence of RACK-1 expression in a melanocytic cell is indicative of the presence of a tumoral cell or of a melanoma, provided that a method having a sensitivity equal or inferior to in situ immunoassay is used for the detection. Indeed, as mentioned above, RACK-1 is expressed in normal melanocytes at a very low level, this protein is thus not detectable in normal melanocytes by using standard methods, for example in situ immunoassay as a detection means, or a detection technique having as sensible or less sensible than in situ immunoassay.

Therefore, in the context of the present invention, immunoassay in situ is a technique particularly preferred for implementing the methods. Indeed, by using immunoassay in situ, the detection of a positive cell for RACK-1 protein is directly indicative of the presence of a tumoral cell and thus of a melanoma.

According to a third embodiment, an object of the present invention is a method for determining the tumoral status of a melanocytic cell of a mammal comprising the steps of determining the level of expression of RACK-1 protein in the melanocytic cell and comparing this level with a reference level.

An increased level of RACK-1 protein expression in said melanocytic cell with respect to the reference level is indicative that this cell is a tumoral cell (tumoral state), preferably a malignant tumoral cell.

The tumoral status of the melanocytic cell under examination is preferably not determined before carrying out the method of the invention. The melanocytic cell is preferably not from an established cell-line. Preferably, the cell under examination is a primary cell.

According to a fourth embodiment, the present invention is directed to a method for diagnosing a melanoma in a mammal comprising the steps of determining the level of RACK-1 protein expression in a melanocytic cell of said mammal and comparing this level with a reference level. An increased level of RACK-1 protein expression in said melanocytic cell with respect to the reference level is indicative of the presence of a melanoma.

The 3rd and 4th embodiments of the invention correspond to the first two embodiments, wherein the determination of expression or overexpression of RACK1 protein expression is made by a comparison to a reference level.

The methods of the invention are preferably carried out in vitro or ex vivo, that is the step of determination of the level of RACK-1 protein is preferably carried out in vitro or ex vivo. Alternatively, it may be carried out in vivo.

In the methods of the invention, the melanocytic cell of a mammal, which is to be analysed for the expression of RACK1 protein, is preferably from a biological sample of said mammal. The reference level, used for the comparison step, is for example the level of RACK-1 protein expression in a non-tumoral, i.e. normal, healthy, melanocyte of the mammal to be diagnosed. The normal melanocyte is for example a normal epidermal melanocyte or a normal choroidal melanocyte. Any other type of normal melanocyte may also be used for the reference level of protein RACK-1 expression.

By an "increased level", it is to be understood that the level is significantly increased, i.e. that the difference between the measured level and the reference level is significant from a statistical point of view, that is the difference is greater that the standard deviation of the measured levels. The difference is thus preferably greater that the error inherent in the measurement and greater than the variations observed between normal melanocytes.

The difference between the measured level and reference level may significantly vary depending on the melanocyte to be analysed and depending on the chosen reference level, the level in a tumoral cell is however greater than the limits of detection, and above the cut-off line. The measured level may be for example at least 5% superior to the reference level, preferably at least 10% or 20% superior, depending on the reference level.

In different embodiments of the invention, the measured level is at least 3 times the reference level, generally at least 6 times, for example at least 10 times higher than the reference level. For example, when the reference level is the level of RACK-1 protein expression in a non-tumoral, i.e. normal healthy, melanocyte, the measured level is at least 1, 5, preferably at least twice the reference level.

The invention also relates to a method for determining the tumoral status of a melanocyte cell in a skin section of a mammal, comprising:

comparing the level of expression of RACK1 protein in said melanocytic cell with the level of expression of RACK1 protein in surrounding keratinocytes in a skin section of said mammal, relating equivalent levels of expression to a tumoral state for said cell.

The invention also relates to a method for diagnosing a cutaneous melanoma in a mammal, comprising:

comparing the level of expression of RACK1 protein in a melanocytic cell with the level of expression of RACK1 protein in the surrounding keratinocytes in a skin section of said mammal, relating equivalent levels of expression to the presence of a cutaneous melanoma.

Such a comparison of the RACK1 protein expression in a melanocytic cell and in keratinocytes on a skin section can be made easily by a person skilled in the art. It is indeed apparent on FIGS. 3 and 4 that on the one hand, expression of RACK1 protein in healthy melanocytes is undetectable whereas it is detectable in surrounding keratinocytes (FIG. 3) and on the other hand, the expression level of RACK1 protein is equivalent in a tumoral melanocyte to that in the surrounding keratinocytes (FIG. 4).

According to the invention, the level of expression of RACK-1 protein may be determined or measured by detection of RACK-1 protein expression and/or estimation of said level of expression.

According to the invention, a melanocytic cell which is to be analysed in order to define its tumoral status, can be from a biopsy. A biopsy according to the invention may be from any organ or tissue. The biopsy is for example a biopsy of skin or eye, or from an inner organ as liver, lymph nodes, lung, heart or spleen.

According to the invention, the level of RACK-1 protein expression is determined by determination of the level of RACK-1 protein in the cell to be diagnosed, or by determination of the level of mRNA corresponding to RACK-1 protein, also in the cell to be diagnosed. Indeed, it has been shown by the present inventors (see the Example section) that the high level of RACK-1 protein in a tumoral melanocytic cell is due to a high level of corresponding mRNA, that is the overexpression of RACK-1 protein is mainly due to an increased level of transcription of the corresponding gene in the tumoral cell.

According to the present invention, the level of RACK-1 protein expression in a cell is advantageously determined by in situ immunoassay. By this technique, it is possible to visualize and measure the level of expression of a peptide or a protein, especially by fluorescence.

Alternatively, when the level of mRNA corresponding to RACK-1 protein is to be determined, an advantageous technique to be employed is in situ hybridisation.

Both in situ hybridisation and in situ immunoassay are well known from the skilled person in the domain of the invention.

For in situ immunoassay, an antibody against RACK-1 is to be used. Such antibodies are commercially available.

With regard to in situ hybridisation, this technique requires the use of a hybridizing probe specific to RACK-1 mRNA. Example of a suitable probe is described in the experimental section of the present description.

The level of RACK-1 expression in a cell may also be determined by RT-PCR on the RNA corresponding to RACK-1 protein.

Alternatively, the presence of RACK-1 protein or the level of RACK-1 protein expression is determined according to the invention, by carrying out an immunological technique, an immunoassay, an immunohistochemistry assay, a confocal microscopy analysis, an ultraviolet spectroscopy, an electrochemical detection or a hybridisation autoradiography.

The immunological technique is preferably a technique employing specific monoclonal or polyclonal antibodies and is preferably selected among an ELISA technique, an immunoenzymatic technique, an immunofluorescence technique, a radio-immunological technique and a chemo-immunological technique. Most preferably the immunological technique is in situ immunoassay with a monoclonal antibody against RACK-1 protein.

Melanoma according to the invention is for example a cutaneous melanoma or a choroidal melanoma.

When the melanocytic cell to be analysed is part of a biopsy of a non-skin tissue normally devoid of melanocyte, the identification of a tumoral cell by the methods of the invention is indicative of a metastasis of a melanoma.

The mammal to be diagnosed according to the invention is preferably a human; however the invention also concerns the diagnosis of tumoral cells of a melanoma in other mammals, especially pets, more preferably pig, horse, cat and dog. Any other mammal is also in the scope of the present invention.

The invention also concerns a method for diagnosing a melanoma in a mammal comprising the steps of bringing a biological sample from said mammal into contact with a means for detecting melanocytic cells and a means for detecting RACK-1 protein expression and determining whether melanocytic cells co-localise with RACK-1 protein expression. The presence of melanocytic cells exhibiting RACK-1 protein expression is indicative of a melanoma. Indeed, in healthy melanocytes, the inventors did not detect any RACK1 protein expression but they detected expression of melanocyte markers. On the other hand, in tumoral melanocytes, the inventors detected expression of RACK1 protein and of melanocyte markers.

The method is preferably carried out in vitro or ex vivo and most preferably in vitro on a biological sample obtained from a mammal to be diagnosed. The diagnostic methods of the invention therefore do not imply any interaction with the human or animal body, necessitating the presence of the latter.

The biological sample used in the implementation of this method is preferably a biopsy from an organ or tissue suspected to host a melanoma or a metastasis of melanoma.

Preferred examples of biopsy are biopsy of lymph node, liver, lung, heart, spleen, eye and skin.

As already mentioned, a means for detecting RACK-1 protein expression is preferably a means for detecting the RACK-1 protein in a sample. Such a means is preferably an antibody, most preferably a monoclonal antibody. Alternatively, it may be a polyclonal antibody. The means for detecting RACK-1 expression may also be a means for determining the mRNA corresponding to RACK-1 protein.

Said means for detecting the RACK-1 expression is advantageously labelled, for example by a fluorescent tag or a radioactive tag. The label may be used to detect and/or to quantify the means for detecting RACK-1.

Said means for detecting melanocytic cells is for example an antibody against the microphthalmia transcription factor MITF, an antibody against the dopachrome tautomerase DCT, an antibody against the tyrosinase TYR, an antibody against the tyrosinase-related protein 1 TRP1 or an antibody against any protein involved in the melanin synthesis pathway. Advantageously, when the means for detecting RACK-1 protein and the means for detecting melanocytes cells are both antibodies, the method is performed by in situ immunoassay with different labels for the two said means (antibodies).

According to the different methods of the invention, the mammal to be diagnosed is preferably a human.

According to the present invention, a preferred mammal to be diagnosed is a human having family history of cancer, or human suspected to be developing a melanoma or suspected to present a high risk of developing such a disease, in particular individuals with blistering or peeling sunburns (especially in the first twenty years of life), fair and red-headed people, persons with multiple atypical nevi or dysplastic nevi, persons born with giant congenital melanocyte nevi and human with a personal or family history of melanoma or of dysplastic nevus syndrome (multiple atypical moles).

In another embodiment of the invention, the mammal to be diagnosed is a pig, a cat, a dog or a horse, or another pets.

It is preferred that the diagnostic methods of the invention are repeated regularly on the diagnosed mammal, especially for a mammal presenting a high risk of developing a melanoma, more preferably for human presenting a predisposition to melanoma. The diagnosis methods of the invention are repeated at least every 3 months, at least every 6 months, once a year or more or less frequently. It is indeed essential to diagnose a melanoma as early as possible in order to begin the treatment at an early stage, before apparition of metastases.

The methods of the invention are preferably carried out in combination with other techniques for diagnosing melanoma. For example, a method of the invention is carried out in order to confirm a first diagnosis made by a different technique, or to confirm a suspicion of melanoma. Alternatively, the methods of the invention may be carried out simultaneously or before other methods allowing the identification of tumoral cells.

The methods of the invention are advantageously used in combination with other diagnosis methods, for example anatomopathological techniques.

In anatomopathology, the tumoral status of a cell may be defined after determination of three different criteria which are mitotic activity, spatial organisation and relation with stroma and blood vessels. Methods of the invention are advantageously carried out in combination with the determination of at least one of these criteria.

The present invention is also directed to a kit for diagnosing a melanoma in a mammal comprising a means for detecting RACK-1 protein expression. As mentioned above, the means for detecting RACK-1 protein expression is preferably a means for detecting the RACK-1 protein. Said means is for example an antibody, preferably a monoclonal antibody; it may also be polyclonal antibodies.

Alternatively, said means may be a means for detecting the level of mRNA corresponding to RACK-1 protein.

A means as used in the kit of the invention, is advantageously labelled, for example by a fluorescent or radioactive label.

A kit as described above preferably further comprises a means for detecting melanocytic cells. A means for detecting melanocytic cells allows the distinction between melanocytic cells and non-melanocytic cells.

Such a means is for example an antibody against the microphthalmia transcription factor MITF, an antibody against the dopachrome tautomerase DCT, an antibody against the tyrosinase TYR, an antibody against the tyrosinase-related protein 1 TRP 1 or an antibody against any protein involved in the melanin synthesis pathway.

Another means may also be envisaged.

Preferably, said further means is also advantageously labelled, for example by a fluorescent or radioactive label. Said label is advantageously different from the label attached to the means for detecting RACK-1 protein expression; for example fluorescent labels with different wavelength emissions.

The invention also relates to the use of RACK1 protein as a marker for the tumoral status, preferably as a marker of a malignant tumoral state, of a melanocyte cell of a mammal, preferably of a human or pets.

Another object of the present invention is the use of the level of expression of RACK1 protein in a melanocyte cell of a mammal, as an indicator of the tumoral status of said cell, preferably as an indicator of a malignant tumoral state.

All the features and preferred embodiments described above in connection with the methods and kits of the invention, also apply to the uses of the invention.

EXAMPLES

Melanoblastoma-bearing Libechov minipigs (MeLiM) exhibit spontaneous malignant cutaneous melanoma. To better understand melanocytes malignant transformation, the inventors compared the serial analysis of gene expression between normal skin melanocytes and melanoma cells from a pulmonary metastasis of MeLiM. Tag identification revealed genes previously not described in melanoma progression. Among them, GNB2L1 was overexpressed in melanoma cells. GNB2L1 encodes RACK1, receptor for activated C kinase (PKC). The inventors studied RACK1 expression in the skin and organs affected by melanoma of MeLiM, by confocal microscopy using MITF as marker of melanocytes. RACK1 was not detected on normal epidermal melanocytes. By contrast, cytoplasmic RACK1 was highly expressed in all melanoma cells of cutaneous tumors and metastases. PKCβII did not colocalise with RACK1 suggesting a role for RACK1 in melanoma malignancy independent of PKCβII signalling. RACK1 was additionally nuclear in metastases. RHEB and β-catenin were also nuclear in metastases but none colocalised with RACK1. High expression of RACK1 was seen in all melanoma cells of cutaneous tumors and metastases in human clinical samples, while RACK1 was not detected in melanocytes of healthy skin. Expression levels of RACK1 in melanoma cells appear to be relevant to their tumoral status.

Melanoma is a malignant tumor developing by transformation of melanocytes. Its incidence and mortality rates in fair-skinned populations increase worldwide. Presence of metastases carries a severe prognosis due to ineffective response to treatments. Understanding the molecular bases of melanoma progression could help developing more effective treatments. Mechanisms of melanocyte transformation are thus widely studied.

In humans, B-RAF is mutated in 66% while INK4a/ARF is deleted in 50% of melanomas (reviewed by Chin (1)). The combination of both lesions leads to activation of the Ras pathway, phosphorylation of the retinoblastoma protein, and increased degradation of TP53. However, these genes do not account for all melanomas, implying the existence of other mechanisms of cell transformation. Global gene expression profiling has been reported on human and murine melanocyte tumor cell lines and samples. Differential expression of RhoC (2), WNT5a (3), Notch2 (4) and genes associated with G proteins and calcium signalling (5), among others, highlighted pathways engaged in cell adhesion and motility as well as tissue invasion in particular cell lines. Overall, melanoma is a complex multigenic disease, and different mechanisms of transformation might be operating.

Among the animal models of the human pathology, the MeLiM (Melanoblastoma-bearing Libechov Minipig) strain affected by cutaneous melanoma seems particularly interesting. Indeed, two month-old MeLiM exhibit spontaneous cutaneous melanoma with metastases in lymph nodes and less frequently in inner organs with histopathological evolution analogous to humans (6). However, the biological relevance of these hereditary pig melanomas to the understanding of predominantly sporadic melanomas in humans is still questionable.

To evaluate whether the MeLiM model could provide valuable information on the progression of the disease in humans, the inventors decided to identify genes involved in the tumoral progression in MeLiM and to assess their expression in human cutaneous melanomas.

The serial analysis of gene expression (SAGE) technology was chosen because, unlike micro arrays, this method gives a complete gene expression profile of cells regardless of the sequences to be analysed. SAGE libraries can be compared in silico to reveal genes specifically expressed in certain cell types (7). To minimise the contribution of cells other than melanocytes, the inventors constructed SAGE libraries from primary melanoma cells cultured from pulmonary melanoma metastasis of MeLiM and from PigMel melanocytes derived from the skin of healthy Meishan minipig (8). It is here reported a comparative analysis of gene expression between malignant and normal melanocytes. The inventors show that RACK1, the receptor of activated C kinase (PKC), is expressed in the cytoplasm of cutaneous tumors and metastases from MeLiM, while its expression is not detected in normal skin melanocytes. Importantly, this differential expression of RACK1 in tumoral and normal melanocytes was also found in clinical specimens from human patients. These results demonstrate a role for RACK1 in the progression of melanoma in mammals. They support the view that the MeLiM strain provides a relevant model to study the complex mechanisms involved in melanoma progression in humans.

Materials and Methods

Pig (*Sus scrofa* Domestica) Tissues.

Affected MeLiM males were mated with healthy Duroc or MeLiM sows at the National Institute for Agricultural Research (INRA, Jouy-en-Josas, France) (6, 9). Animal care and use were approved by the INRA ethics council, in accordance with European Union standards. Biopsies from 3 month-old or younger MeLiM, bred either in France (n=13) or in the Czech Republic (n=3), were used. They included cutaneous melanoma consisting of superficial spreading melanoma (n=2) and nodular melanoma (n=7) and metastases in lymph nodes (n=13), lung (n=10), liver (n=1), heart (n=2) and spleen (n=3), as well as healthy skin (n=10). Samples of dorsal cervical skin of a healthy pigmented Meishan were used as controls. Collected tissues were fixed in 4% buffered paraformaldehyde (PFA) and embedded in paraffin.

Isolation of Metastatic Melanoma Cells and Culture of Control Melanocytes.

Tumor biopsies of lung from a young MeLiM were used to isolate melanoma cells. Conditions for primary cultures of pig melanocyte cells were as described (8). Tetradecanoylphorbol-acetate was added the second day of culture. After 48 hours cells were rinsed, lysed in Dynabead mRNA direct kit binding buffer (Dynal, Invitrogen Life Technologies, Cergy Pontoise, France) and frozen in liquid nitrogen. Control melanocytes were the non transformed PigMel cells at passage 37 (8).

Construction of SAGE Libraries.

Libraries were generated using the SAGE adaptation for downsized extracts (SADE) method (10) with a centrifugation of cell lysates to discard melanin. Sequencing reactions were performed by MWG (Martinsried, Germany).

Tag Identification and Cloning of the Probes.

SAGE tags were extracted from sequence files using the SAGE 2002 version 4.5 software (7). Statistical significance was determined using Monte-Carlo simulation analysis. A P value of 0.05 or less was considered significant. Tags were identified using the mammalian Genbank database analysed by the SAGE software, or the AGENAE EST database. Pig RACK1 partial cDNA corresponding to the nucleotide sequence −70 to 900 bp from the ATG start codon was subcloned into pCR4TOPO plasmid (Invitrogen™ Life Technologies™). The resulting plasmid was linearized either with NotI or PmeI to obtain sense or antisense RNA probes, respectively. In vitro transcription was performed as described (11).

In Situ Hybridisation of Heavily Pigmented Samples.

In situ hybridisation was performed as described (12) with modifications to bleach the sections. Briefly, deparaffinized 5 µm sections were treated for 15 minutes with 0.075% KMnO4 and decoloured 1 minute in 5% oxalic acid with brief rinses between and after treatments. Sections were fixed for 20 minutes in 4% PFA, rinsed, dehydrated and air-dried. Sense or antisense radiolabeled riboprobes at about $15 \times 10^6$ cpm/ml were hybridised as described (11). Slides were exposed to Biomax MR films (Kodak, France) for 3 days, then dipped in Kodak NTB2 emulsion and exposed for 4 weeks.

Human Tissues.

Human melanoma tissues were obtained at the Curie Institute (Paris, France) from patients undergoing lymphadenectomy (n=13), hepatectomy (n=5) or epidermal cutaneous resection (n=19). Cutaneous melanoma specimens consisted of 2 superficial spreading melanoma stages 1V (Breslow depth of 2.35 and 2.5 cm) and 3 recurrent dermal cutaneous melanoma. Samples from 37 patients, 25 women and 12 men, were examined.

Normal skin from a breast plastic surgery was used as control (n=4).

Tissues were fixed either in 4% PFA (n=38) or in Bouin fixative (n=2) and embedded in paraffin.

Antibodies (Dilutions for Immunolabelling).

Mouse monoclonal antibodies used were anti-MITF (1:50) (clone C5+D5, Zymed, Clinisciences, Montrouge, France), anti-RACK1 (1:150) and anti-β-catenin (1:100) (Transduction Laboratories, BD Biosciences, Le Pont de Claix, France), and the polyclonals PEP-8 anti-DCT (1:1000), anti-RHEB (1:100) and anti-PKCβll (1:200) (Santa Cruz Biotechnology, Tebu-bio, Le Perray, France). Cross reaction and specificity of the antibodies to pig tissue were checked by Western blot.

For assays on equine samples, the MITF antibody (C5+D5, Zymed) was diluted 1:100, and molecular grade BSA 0.1 mg/ml was added to normal goat serum in every step.

Immunostaining and Confocal Microscopy.

Antigen retrieval was performed by microwaving deparaffinized sections in citrate buffer, pH 6, for pig sections, and in Tris-EDTA, pH 9, 0.05% Tween 20 for human sections. For immunohistochemistry, primary antibodies were reacted with the avidin-biotin complex (ABC Elite, Vector, Biovalley, France). For double immunofluorescence, antibodies applied overnight at 4° C. were revealed with anti-mouse isotype or anti-rabbit antibodies, one labelled with Alexa Fluor 555, the other coupled to biotin and revealed with Alexa Fluor 488 labelled streptavidin (Molecular Probes, Invitrogen Life Technologies, France). Nuclear counterstaining was achieved with Topro 3 (Molecular probes). Sections were observed with a Leica laser TCS SP2 scanning confocal microscope producing 0.7 µm-thick optical sections. Controls without the first antibodies showed no unspecific labelling. Confocal images were processed with the computer program Leica Lite or Zeiss LSM Image Browser for orthogonal projections. All images shown are individual sections of z series, plus the orthogonal projections of the stack when indicated. Final figures were assembled with Adobe Photoshop (Adobe Systems, USA).

Results

Characterisation of Metastatic Melanoma from MeLiM.

Figures 1, 1B, 2:
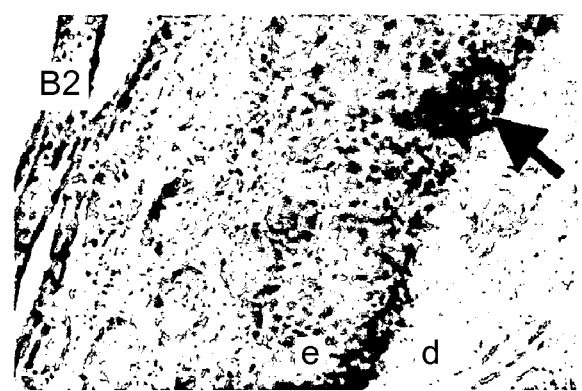
Figures 1, 1C:
FIG. 1 B1-D1: identification of melanocytes by immunohistochemistry with MITF antibody, visualized as brown nuclear granules.
Figures 1, 1C, 2:
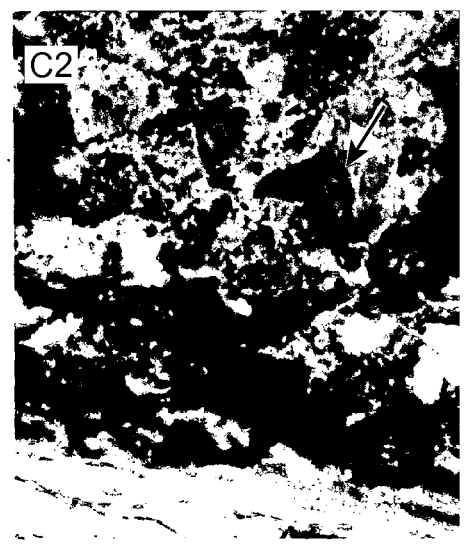
Figures 1, 1D:
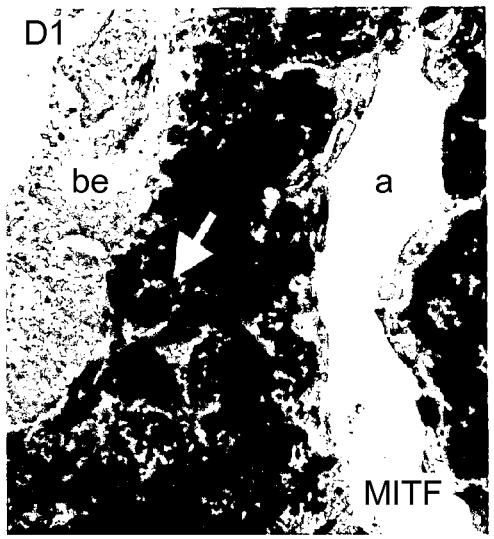
Figures 1, 1D, 2:
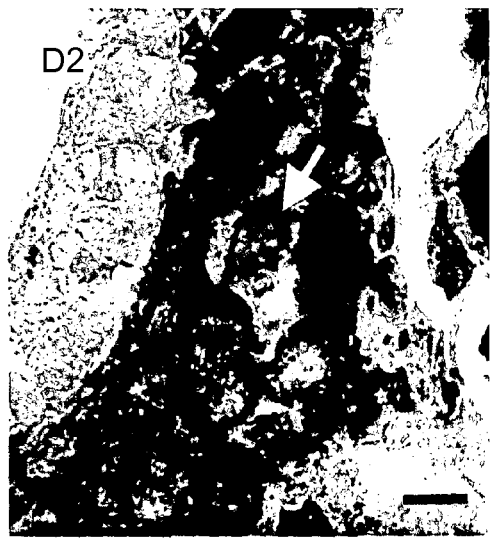

Young MeLiM developed melanoma metastases in lymph nodes, liver, heart and lung illustrated in FIG. 1A On tissue sections, identification of melanoma cells was achieved with an antibody against the microphthalmia transcription factor MITF, which produces a specific nuclear signal in melanocytes, immunohistochemistry shows a normal melanocyte in the basal layer of control skin epidermis, labelled for MITF (FIG. 1B1). Tumoral cells in cutaneous melanoma as well as in metastases were also labelled with the MITF antibody (FIG. 1C1-D1). Unspecific label was not detected with this antibody (FIG. 1B2-D2). Thus, MITF is a sensitive marker of the melanocyte lineage, useful to study melanoma progression in the pig.

Comparative Expression Analysis Between Metastatic Melanoma Cells and Melanocytes.

To isolate melanoma cells from lung metastases, primary cultures of tumors were performed in conditions optimised for pig melanocyte proliferation (8). After 48 hours in culture, adherent cells were predominantly melanocytes. SAGE libraries were constructed from 2.5 millions of these metastatic melanoma cells (MMC) and PigMel normal melanocytes (NM). A total of 11,300 and 11,700 tags were sequenced from the NM and MMC libraries, corresponding to 5,466 and 6,131 different tags (transcripts), respectively. Seventy tags were differentially represented (P<0.05) in the two libraries. Fifty-four (77%) matched expressed sequence tags, from which 37 (53%) matched to known cDNAs. A majority of tags matched genes expressed at high levels. The identified genes are involved in RNA processing and protein synthesis (20%), transcription (7%) or signalling (4%). The list of tags increased and decreased in MMC compared to NM, arbitrarily ordered by functional classes of the genes they represent, are shown in Tables 1 and 2, respectively. The mRNA of GNB2L1 corresponded to a tag abundant 31 and 13 counts in MMC and NM, respectively.

Tag Seq:

(SEQ ID No. 1)

ATTGTAGATG.

The inventors chose to study GNB2L1 expression in melanocytes and melanomas in more detail because it encodes RACK1 (NM_214332, which is identical to the human RACK-1 P63244 SEQ ID No. 69), receptor for activated C kinase, which mRNA has been found up-regulated in human carcinomas (13).

TABLE 1

SAGE tags significantly increased in metastatic melanoma cells (MMC) compared to normal melanocytes (NM) (p < 0.05).

| Tag sequence | NM | MMC | GenBank match (accession number) |
|---|---|---|---|
| Translation, ribosomal structure and biogenesis | | | |
| ACATCCATCA (SEQ ID NO. 2) | 28 | 73 | Ss 40S ribosomal protein S20 RPS20 (AY550070) |
| AAACCAAAGA (SEQ ID NO. 3) | 1 | 10 | Ss cDNA (AJ681350)homolog to Hs small nuclear ribonucleoprotein polypeptides B and B1, SNRPB (BC080516) |

TABLE 1-continued

SAGE tags significantly increased in metastatic melanoma cells (MMC) compared to normal melanocytes (NM) ($p < 0.05$).

| Tag sequence | NM | MMC | GenBank match (accession number) |
|---|---|---|---|
| TGACTATAAC (SEQ ID NO. 4) | 18 | 35 | Ss cDNA (BX923125) homolog to Hs ribosomal protein L24, RPL24 (BC000690) |
| AAGTTCCCGC (SEQ ID NO. 5) | 17 | 32 | Ss cDNA (BX674755) homolog to Hs ribosomal protein L18a, RPL18A (BC066319) |
| AACCTAATTA (SEQ ID NO. 6) | 58 | 77 | Ss 40S ribosomal protein S12, RPS12 (NM_214363) |
| AACTCAATAA (SEQ ID NO. 7) | 44 | 62 | Ss cDNA (BX914485) homolog to Hs ribosomal protein L10a, RPL10A (NM_007104) |
| AAAGATTAAG (SEQ ID NO. 8) | 20 | 32 | Ss cDNA (BX921758) homolog to Hs ribosomal protein L27, RPL27 (L05094) |
| Signal transduction mechanisms | | | |
| ATTGTAGATG (SEQ ID NO. 1) | 13 | 31 | Ss guanine nucleotide beta like protein GNB2L1, RACK1 (NM_214332) |
| AGTTATGAAG (SEQ ID NO. 9) | 0 | 5 | Ss cDNA (CN160727) homolog to Hs ras-related GTPbinding protein, Rheb (D78132) |
| AAGCTACACA (SEQ ID NO. 10) | 4 | 11 | Ss cDNA (CJ016486) homolog to Hs calmodulin 1 (phosphorylase kinase, delta), CALM1 (BC011834) |
| Transcription | | | |
| CAGAGGGAGA (SEQ ID NO. 11) | 1 | 10 | Ss cDNA (CN 157150) homolog to Hs retinoblastoma binding protein, RbAp48 (X74262) |
| ACAACTGGGG (SEQ ID NO. 12) | 0 | 6 | Ss cDNA (BX675828) homolog to Hs general transcription factor IIB, GTF2B (NM_001514) |
| TGATAGAAGA (SEQ ID NO. 13) | 6 | 15 | Ss cDNA (CF792678) homolog to Hs activating transcription factor 4, ATF4 (BC073754) |
| TATGAATAAG (SEQ ID NO. 14) | 4 | 11 | Ss cDNA (AJ666570) homolog to Hs c-myc transcription factor puf, NM23H2 NDPK (L16785) |
| Secondary metabolites biosynthesis, transport and catabolism | | | |
| AGTATCAACA (SEQ ID NO. 15) | 24 | 46 | Ss TYRP1 tyrosinase related protein1 (AB207240) |
| Secretion | | | |
| TGCTCAGGCT (SEQ ID NO. 16) | 0 | 13 | Ss cDNA (BX674961) homolog to secernin |
| Energy production and conversion | | | |
| AATACAAGTT (SEQ ID NO. 17) | 3 | 12 | Ss cDNA (BX675828) homolog to Bos taurus MLRQ subunit of NADH: ubiquinone oxidoreductase complex (X64897) |
| Post-translational modification; protein turnover | | | |
| GAGGTGGAGA (SEQ ID NO. 18) | 3 | 10 | Ss cDNA (CJ014518) homolog to Hs peptidylprolyl isomerase B (cyclophilin B), PPIB (NM_000942) |
| General production only | | | |
| ATTTCTAGGC (SEQ ID NO. 19) | 0 | 5 | Ss cDNA (CK455473) homolog to Hs CDC10 cell division cycle 10 homolog (*S. cerevisiae*), CDC10 (NM_001788) |
| Function unknown | | | |
| TCACCCGCAA (SEQ ID NO. 20) | 0 | 9 | No reliable matches |
| TCGTCCCTGT (SEQ ID NO. 21) | 0 | 8 | Ss cDNA (BX665592) |
| CCTGTGCTGA (SEQ ID NO. 22) | 0 | 7 | Ss-cDNA (AJ6447874) |
| GGTCATTCAT (SEQ ID NO. 23) | 0 | 7 | No reliable matches |
| TCGCCTGGAG (SEQ ID NO. 24) | 0 | 7 | No reliable matches |

TABLE 1-continued

SAGE tags significantly increased in metastatic melanoma cells (MMC) compared to normal melanocytes (NM) (p < 0.05).

| Tag sequence | NM | MMC | GenBank match (accession number) |
|---|---|---|---|
| TCGTCCCTTC (SEQ ID NO. 25) | 0 | 7 | No reliable matches |
| ATTCATGTCA (SEQ ID NO. 26) | 3 | 13 | Ss cDNA (BP164587) |
| GTCTAATCAC (SEQ ID NO. 27) | 2 | 10 | No reliable matches |
| AATGACCGAC (SEQ ID NO. 28) | 0 | 6 | No reliable matches |
| CACCCGCAAT (SEQ ID NO. 29) | 0 | 6 | No reliable matches |
| CCTTCCGACT (SEQ ID NO. 30) | 0 | 6 | No reliable matches |
| CGTCCCTGTG (SEQ ID NO. 31) | 0 | 6 | No reliable matches |
| AGATAATTTG (SEQ ID NO. 32) | 0 | 5 | Ss cDNA clone (AJ65780) |
| ATAGACGAGC (SEQ ID NO. 33) | 0 | 5 | No reliable matches |
| CTGCATTGCT (SEQ ID NO. 34) | 1 | 7 | Ss cDNA (BX922537) |
| AGAATATAAG (SEQ ID NO. 35) | 5 | 13 | No reliable matches |
| CCGCGTTGCT (SEQ ID NO. 36) | 41 | 57 | Ss cDNA (AJ666089) |
| ATGAAGATAT (SEQ ID NO. 37) | 2 | 8 | Ss cDNA (CB286104) |
| TGCTGCAGGG (SEQ ID NO. 36) | 4 | 11 | Ss cDNA (CA780804) |

TABLE 2

SAGE tags significantly decreased in metastatic melanoma cells (MMC) compared to normal melanocytes (NM) (p < 0.05)

| Tag sequence | NM | MMC | GenBank match (accession number) |
|---|---|---|---|
| Translation, ribosomal structure and biogenesis | | | |
| GTCGTTCTGG (SEQ ID NO. 39) | 52 | 29 | Ss cDNA (BX920790) homolog to Hs eukaryotic translation elongation factor 1 alpha 1 (BC020477) |
| AGACTTTTAA (SEQ ID NO. 40) | 6 | 0 | Ss cDNA (BX923125) homolog to Hs ribosomal protein L24, RPL24 (BC070193) |
| GACTTTGACA (SEQ ID NO. 41) | 6 | 0 | Ss cDNA (BX676185) homolog to Hs eukaryotic translation initiation factor 3 subunit k, eIF3k (AY245432) |
| TCTGGAAAGA (SEQ ID NO. 42) | 24 | 11 | Ss cDNA (BX675247) homolog to Hs ribosomal protein S2, RPS2 (BC019021) |
| TCTGACTACC (SEQ ID NO. 43) | 5 | 0 | Ss cDNA (BX922533) homolog to Hs mitochondrial ribosomal protein L40, MRPL40 (NM_003776) |
| AGAAAGCTGT (SEQ ID NO. 44) | 9 | 2 | cDNA (CJ010791) homolog to Hs ribosomal protein L6, RPL6 (BC071912) |
| AGCGTTGAGC (SEQ ID NO. 45) | 39 | 23 | Ss 40S ribosomal protein S16, RPS16 (AY550068) |
| Transcription | | | |
| AGGGGAAATG (SEQ ID NO. 46) | 11 | 3 | Ss cDNA (BX665090) homolog to Hs small nuclear nibonucleoprotein D3, (BC034447) |
| Secondary metabolites biosynthesis | | | |
| ACCCTGGCTG (SEQ ID NO. 47) | 90 | 46 | Ss cDNA (BX 920958) homolog to Equus caballus melanocyte protein 17 precursor, PMEL17 (AF076780) |

TABLE 2-continued

SAGE tags significantly decreased in metastatic melanoma cells (MMC) compared to normal melanocytes (NM) (p < 0.05)

| Tag sequence | NM | MMC | GenBank match (accession number) |
|---|---|---|---|
| Energy production and conversion | | | |
| CTAAAAAAAA (SEQ ID NO. 48) | 18 | 5 | Ss mitochondrial COX III (AJ953126) |
| TCAGAAGAGA (SEQ ID NO. 49) | 15 | 4 | Ss cDNA (CN155299) homolog to Hs ATP synthase, H+ transporting, mitochondrial F1 complex, a subunit, isoform 1, ATP5A1 (BC008028) |
| TCACCTGGGG (SEQ ID NO. 50) | 9 | 2 | Ss cDNA (CB477260) homolog to Hs ATP synthase, H+ transporting, mitochondrial F1 complex, epsilon subunit, ATPE BC003671) |
| Cell division | | | |
| CCCAACAATG (SEQ ID NO. 51) | 5 | 0 | Ss cDNA (BP143055) homolog to Hs beta-tubulin, (AF141349) |
| Post-translational modification, protein turnover | | | |
| TCTAAAGCGG (SEQ ID NO. 52) | 7 | 0 | Ss cDNA (BX672659) homolog to Hs glucose regulated protein 58KD, GRP58 (NM_005313) |
| AGTGGCTTTG (SEQ ID NO. 53) | 7 | 1 | Ss cDNA (CJ007805) homolog to Hs proteasome (prosome, macropain) subunit, beta type, 4, HsN3 (BC008314) |
| General prediction only | | | |
| AGCATCCAGA (SEQ ID NO. 54) | 5 | 0 | Ss cDNA (BX925627) homolog to Hs nuclear distribution gene C homolog, NUDC (NM_006600) |
| CAGAGCTGCC (SEQ ID NO. 55) | 5 | 0 | Ss cDNA (CK459123) homolog to Hs SET binding factor 1, SBF1 (NM_002972) |
| CTAGACGACT (SEQ ID NO. 56) | 7 | 1 | Ss cDNA (BX676609) homolog to HS arginine-rich, mutated in early stage tumors, ARMET (NM_006010) |
| Function unknown | | | |
| AGATGGCCAG (SEQ ID NO. 57) | 7 | 0 | No reliable matches |
| AGCTTAAGCA (SEQ ID NO. 58) | 6 | 0 | Ss cDNA (BX922388) |
| ATGTGCCTGG (SEQ ID NO. 59) | 6 | 0 | Ss cDNA (BX674457) |
| TATGGGGGTC (SEQ ID NO. 60) | 6 | 0 | No reliable matches |
| TGTCAAAAAA (SEQ ID NO. 61) | 22 | 9 | Ss cDNA (BX926374) |
| AGCCTGGACC (SEQ ID NO. 62) | 5 | 0 | No reliable matches |
| AGGGAATGGA (SEQ ID NO. 63) | 5 | 0 | Ss cDNA (BX674961) |
| CCTAGCCTGG (SEQ ID NO. 64) | 5 | 0 | Ss cDNA (CN163385)) |
| TGGCATGGCT (SEQ ID NO. 65) | 5 | 0 | Ss cDNA (BX920198) |
| CACTGCTCAA (SEQ ID NO. 66) | 16 | 6 | Ss cDNA (BX919322) |
| AGCTGTTCTA (SEQ ID NO. 67) | 11 | 3 | Ss cDNA (BX670542) |
| CACCCGCAAT (SEQ ID NO. 68) | 9 | 2 | No reliable matches |

RACK1 mRNA Overexpression in Melanoma.

Figure 2A:
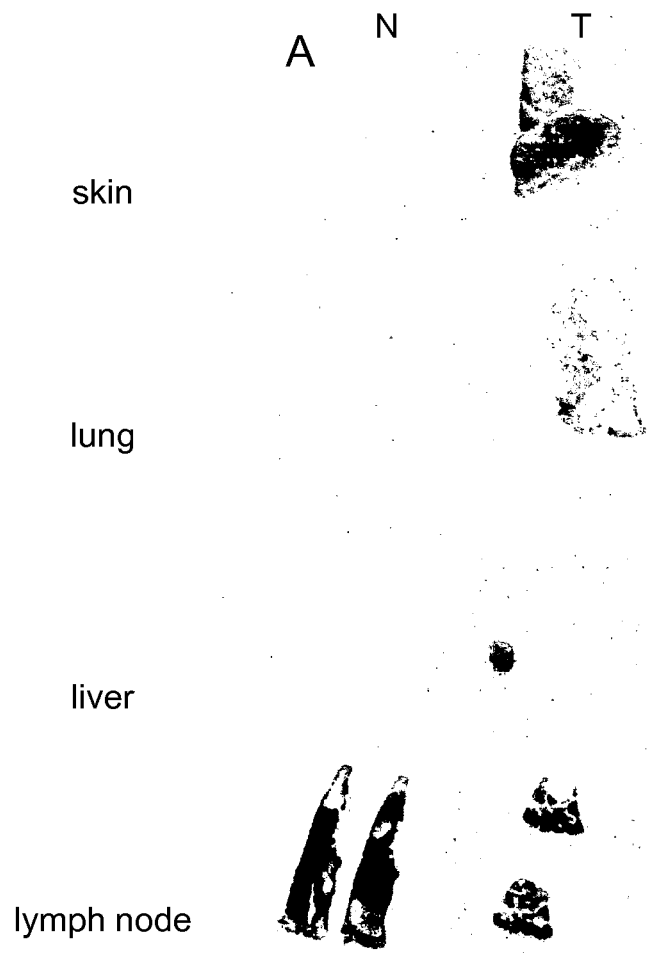
Figure 2B:
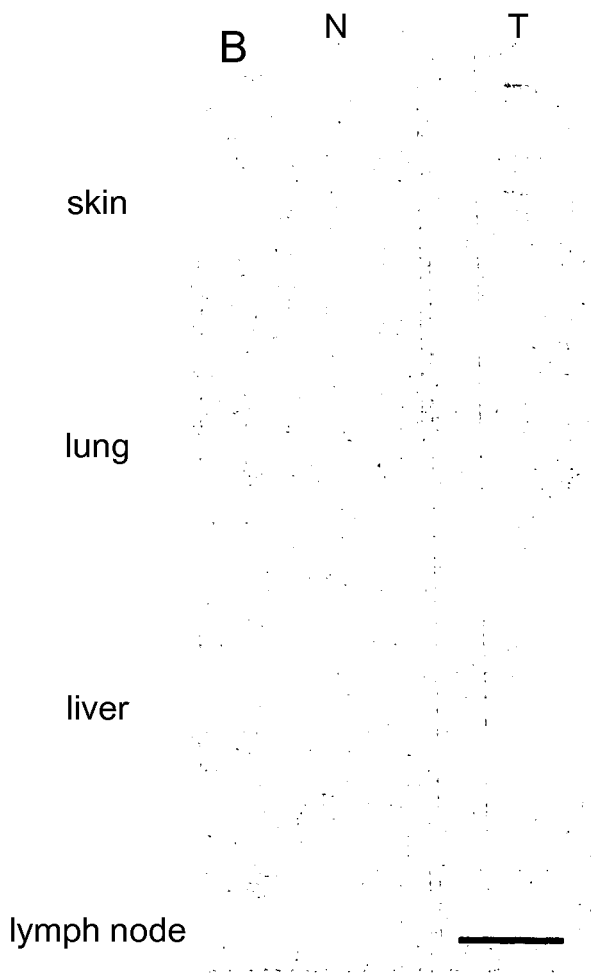
Figure 2C:
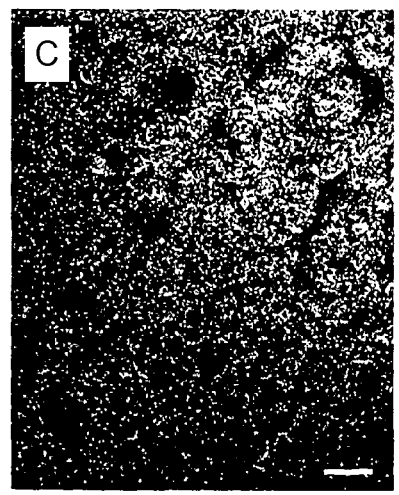
Figure 2D:
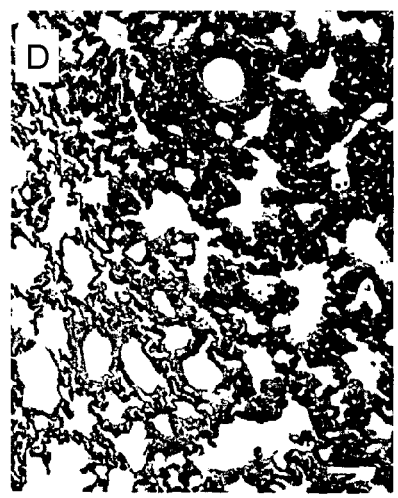

To define the distribution pattern of RACK1 mRNA, the inventors performed in situ hybridisation onto pig sections of normal skin cutaneous melanoma and metastatic melanoma samples from lung, liver and lymph nodes. To avoid background on heavily melanogenic tumor areas, a bleaching treatment was added which oxidised melanin, while preserving mRNA. Film autoradiography obtained with the antisense and sense probes showed a faint signal of RACK1 mRNA in healthy tissues, except for the lymph nodes where the signal was strong (FIG. 2A), as reported on human lymph nodes (13). By contrast, an intense signal was observed in tumoral regions of cutaneous melanoma, lung and liver metastasis samples; nontumoral regions displayed a much lower signal (FIG. 2A). Sense probe autoradiographic signal was almost negligible (FIG. 2B). Darkfield illumination on emulsion autoradiography highlighted the silver grains on the tumoral region of lung melanoma (FIG. 2C). These results confirmed RACK1 mRNA overexpression in melanoma as predicted by the SAGE data.

RACK1 Protein Localisation in Melanocytes from Skin and During Melanoma Progression in Pigs.

To explore whether overexpression of RACK1 mRNA had functional significance, the inventors analysed RACK1 cellular distribution by confocal microscopy, with double immunostaining using MITF as a marker of melanocytes.

The inventors first analysed control Meishan and healthy MeLiM skins, i.e. RACK1 expression in normal pig epidermis, by confocal microscopy analysis of RACK1 protein (fluorescently labelled in green), and double labelling for MITF or DCT on pig skin. The inventors observed a RACK1 cytosolic spotty signal on keratinocytes and its absence in the melanocytes (FIG. 3).

Figure 3A:
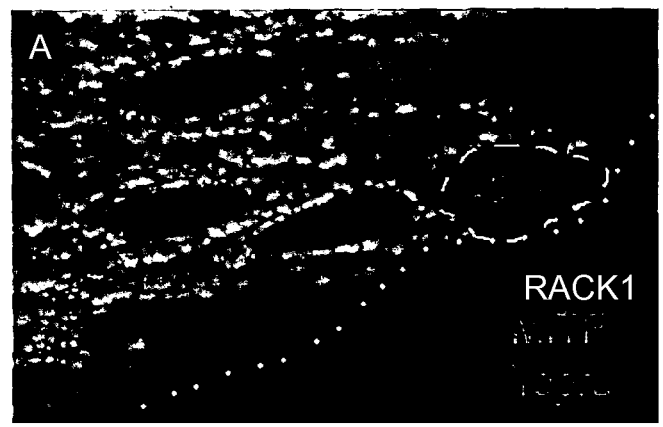
Figure 3B:
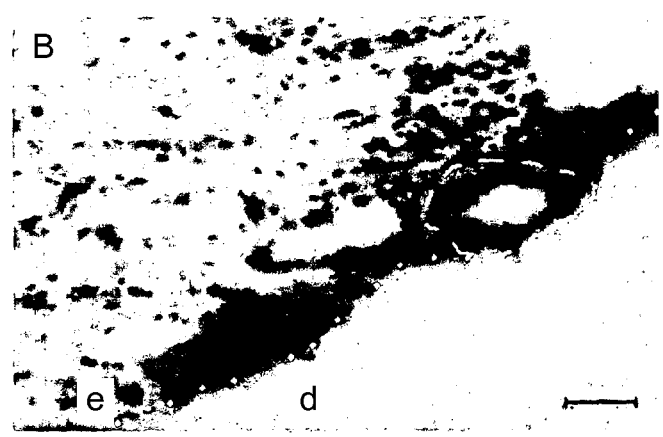
Figure 3C:
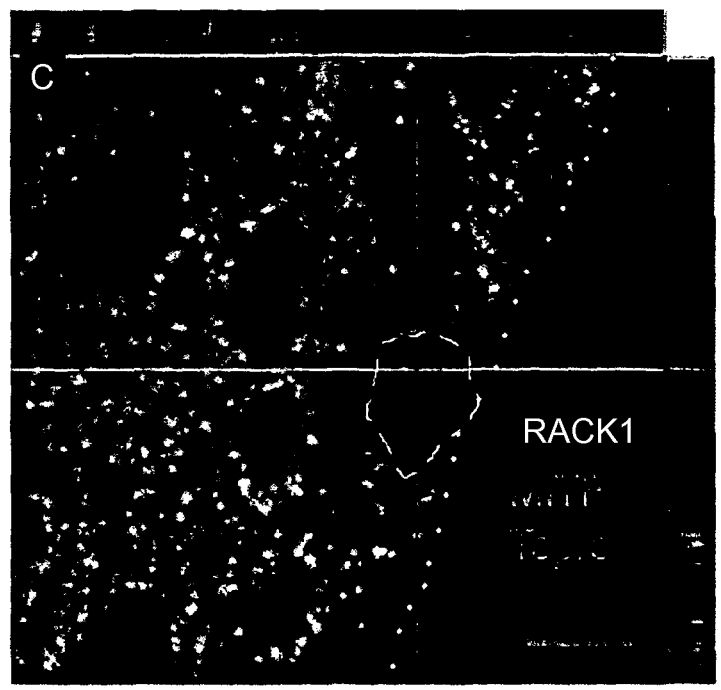
Figure 3D:
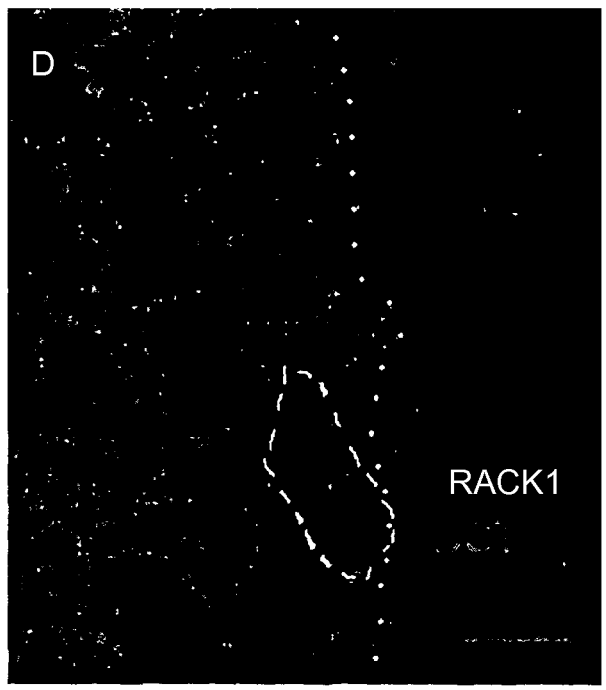

RACK1 protein was expressed in the epidermis, largely localised to the cytoplasm in keratinocytes (FIG. 3A-D). In MITF-positive melanocytes of Meishan and MeLiM skins, RACK1 expression was not detected (FIG. 3A,C). Consistent with this, when testing dopachrome tautomerase (DCT), an enzyme restricted to melanosomes, double labelling of RACK1 and DCT was clearly not overlapping in normal skin (FIG. 3D).

Next, the inventors analysed tumoral tissues (FIG. 4), specifically the cellular distribution of RACK1 in MeLiM melanoma at different progression stages, by confocal microscopy analysis of RACK1 protein (green), and double labelling for MITF (red). The tissues analyzed are a: cutaneous melanoma and melanoma metastasis in a lymph node, lung and heart. It is to be noted the comparable RACK1 cytosolic signal on dermal melanoma cells and epidermal keratinocytes. RACK1 is abundant in cutaneous and metastatic melanoma cells with perinuclear localization. Furthermore, in metastases, nuclear RACK1 is present.

In cutaneous melanoma, nests of pigmented MITF-positive cells expressed RACK1 protein as strongly as epidermal keratinocytes (FIG. 4A). RACK1 localised to the cytoplasm, mostly in the perinuclear area (FIG. 4A3). In lymph node, lung and heart melanoma metastases, RACK1 protein was abundant on MITF-positive cells. Subcellular distribution of RACK1 was cytoplasmic. However, an additional labelling to nuclear punctae was observed in 15% of MMC (FIG. 4B-D, yellow arrowheads).

Thus, RACK1 overexpression in tumoral tissues is observed cytoplasmic in melanoma cells at different progression stages, with an additional nuclear localisation in MMC (metastatic melanoma cells).

Putative Partners of RACK1 in Pig Melanoma Cells.

To explore the molecular mechanism of RACK1 action, the inventors searched for partners of RACK1 protein in melanoma cells. RACK1 has been identified as an intracellular receptor for PKCβll (14). The inventors studied PKCβll expression during melanoma progression.

Figures 1, 5A:
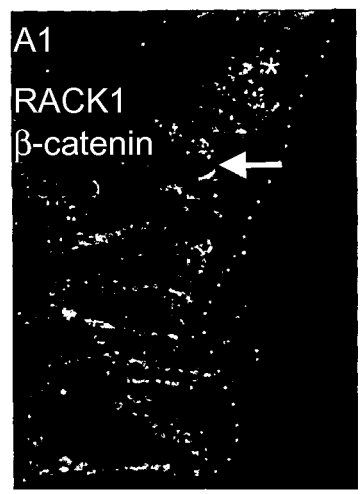
Figures 2, 5A:

PKCβll immunofluorescence showed a weak cytoplasmic signal in NM (normal melanocytes); MMC showed additional discrete nuclear dots, although no overlapping fluorescence was detectable with RACK1. For comparison, a strong PKCβll signal overlapping with RACK1 signal was detected in tissue lymphocytes. This suggests that melanocyte cells do not express abundant PKCβ11.

β-catenin mutations are thought to play some role in melanoma (15), and β-catenin is important in cell adhesion. The inventors therefore examined β-catenin localisation in normal melanocytes and melanoma cells from MeLiM by confocal microscopy and its respective transmission image on normal skin and melanoma metastasis in lung after double labelling of RACK1 (red) and β-catenin (green), β-catenin was ubiquitously expressed and localised to the cell membrane in normal pig epidermis (FIG. 5A).

Figures 1, 5B:
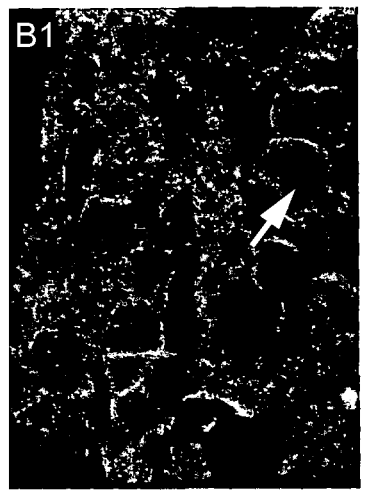
Figures 2, 5B:

In MMC, membranous and cytoplasmic β-catenin signals were often visible together with a nuclear labelling. However, β-catenin and RACK1 signals did not colocalise within the nucleus (FIG. 5B).

Figures 1, 5C:
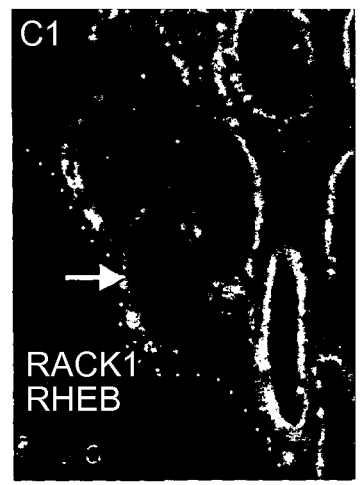
Figures 2, 5C:
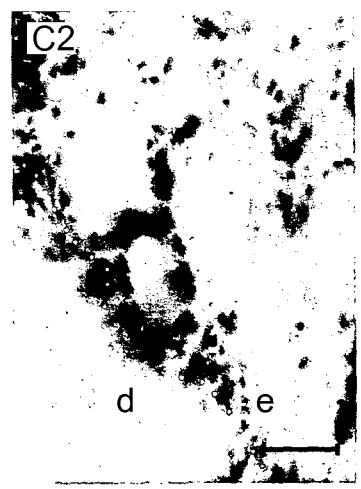
Figures 1, 5D:
Figures 2, 5D:

Another tag overexpressed in MMC in the present SAGE study was identified as RHEB encoding Ras homolog enriched in brain, a member of the Ras superfamily of small GTPase. RHEB plays a key role in the regulation of cell growth in response to growth factors, nutrients and amino acids linking PI3K and target of rapamycin (TOR) signalling (16). Hence, the inventors examined RHEB localisation in MeLiM tumors. RHEB signal was perinuclear in NM but appeared diffuse and nuclear on MMC (FIG. 5C-D). No colocalization was seen with RACK1 signal in melanocytes and tumor cells.

These results suggest that β-catenin, RHEB and PKCβ II are not the major functional partners for RACK1 during melanoma progression.

RACK1 Protein Localisation in Human Skin and Melanoma Samples.

Figure 6A:
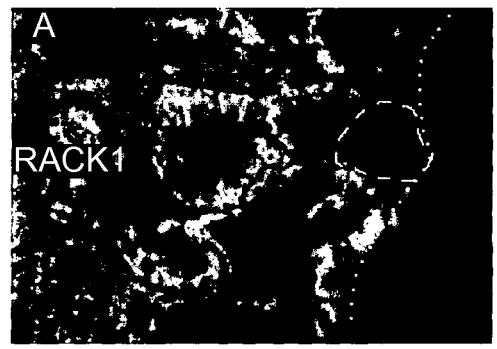
Figure 6B:
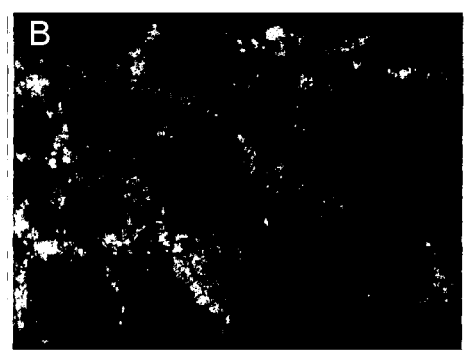
Figure 6C:
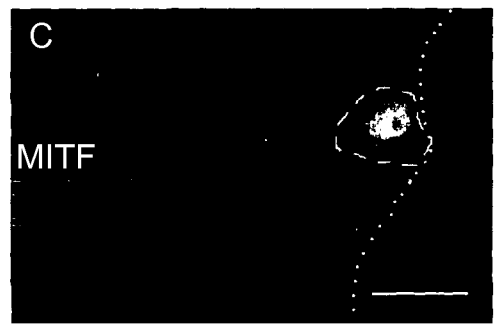
Figure 6D:
Figure 6E:
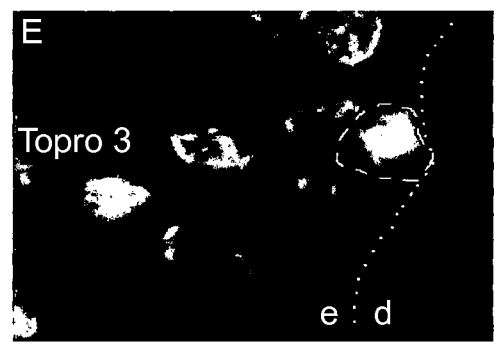
Figure 6F:

Finally, the inventors examined whether overexpression of RACK1 occurred also in human melanoma samples using MITF as marker of human melanocytes and melanoma cells (17). In normal skin, RACK1 was barely detected in melanocytes in contrast to keratinocytes (FIG. 6A), by confocal microscopy analysis of RACK1 protein, with double labelling for MITF (FIG. 6C) or with nuclear counterstaining with Topro 3 (FIG. 6E). In cutaneous melanoma and metastases of melanoma in lymph nodes and liver, MITF-positive cells presented a strong granular cytoplasmic pattern of RACK1 underlying cell shape. RACK1 overexpression was consistently observed in each of the 20 samples examined (FIGS. 6B, D and F). No nuclear RACK1 labelling was found in these melanoma samples.

Comparison of RACK1 Expression in Human Melanoma and Nevi.

To further investigate the expression of RACK1 in human melanoma, the inventors ascertained its presence in a series of samples. Formalin fixed tissue from 4 normal skin biopsies, 14 nevi and 5 cutaneous melanoma were analysed using MITF as melanocyte marker (17).

The results are summarized in Table 3.

TABLE 3

RACK1 level expression and localisation in normal skin,, nevi and melanoma from patients..

| | | | RACK1 expression level | | |
|---|---|---|---|---|---|
| Tissue type | Age of patient (year-old) | Nb of specimens examined | Undetected or faint membranous | Low cyto-plasmic | High cyto-plasmic |
| Normal skin melanocytes | | 4 | 4 | 0 | 0 |
| Benign nevi | 26 to 73 | 14 | 7 | 7 | 0 |
| Cutaneous melanoma | 34 to 79 | 5 | 0 | 0 | 5 |

Figure 7A:
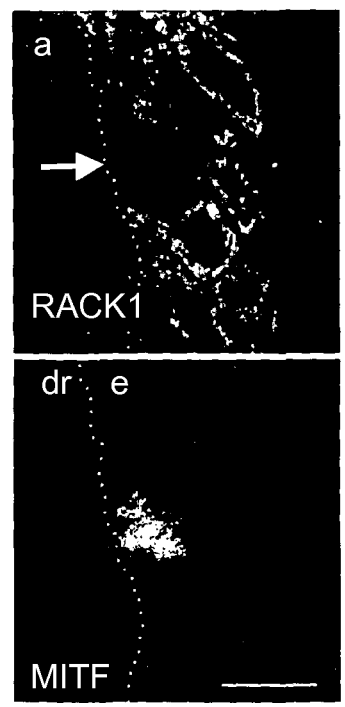
Figure 7B:
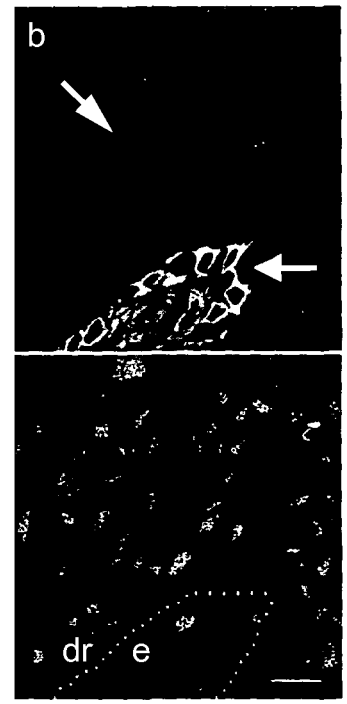
Figure 7C:
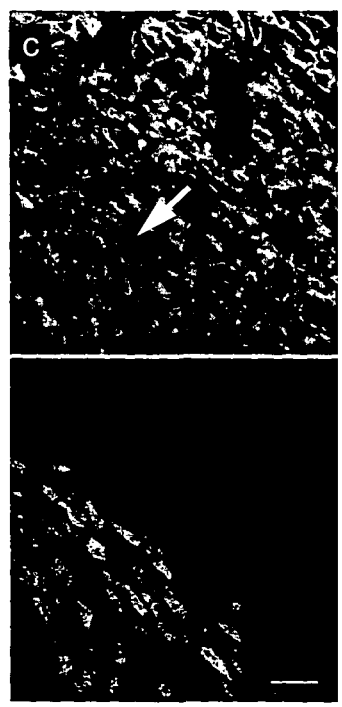
Figure 7D:
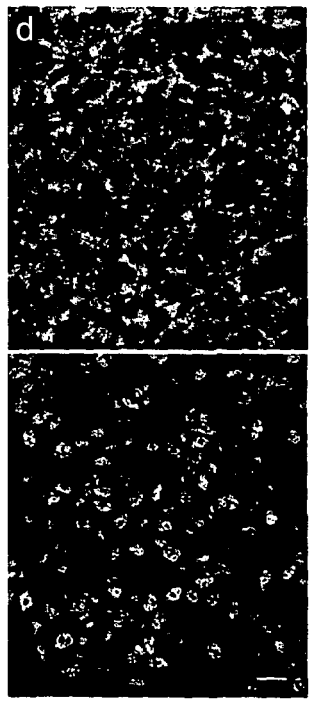

In normal skin, RACK1 was present in negligible amounts in melanocytes whereas adjacent keratinocytes displayed a strong cytoplasmic signal (FIG. 7A). In nevi, RACK1 signal was heterogeneous within a given nevus and between nevi showing two patterns: in 7 out of 14 nevi, RACK1 signal was either not detectable (arrowheads, FIG. 7B) or faint (arrow, FIG. 7B). When detected in epidermal or dermal melanocytes, the signal was essentially membranous.

Taken together, these results show that RACK1 mRNA and protein are up-regulated in human melanomas as found in pig melanomas indicating a correlation between the melanoma tumoral status and high levels of RACK1.

RACK1 Overexpression in Choroidal Melanoma.

Choroidal melanoma (or uveal melanoma) is the most common form of malignant eye tumour in human. A chromosome 3 monosomy, a rare chromosomal abnormality in tumors, has been detected in nearly half of uveal melanoma. Chromosome 3 monosomy is correlated with tumoral malignancy [38].

The inventors have analysed histology slides made from enucleation products on uveal melanoma with and without chromosome 3 monosomy (N=6). The analysis has been carried out by essentially the same protocol as described above.

RACK1 is expressed at high levels in all tumoral melanocytes of both types of uveal melanoma, with chromosome 3 monosomy (as illustrated in FIG. 8) and without chromosome 3 monosomy.

RACK1 Expression in Equine Melanoma.

The inventors have observed that RACK1 is not expressed at a detectable level in normal melanocytes of healthy skin in horses.

They have also examined RACK1 expression in 6 samples from malignant tumors. They were all positive for RACK1 expression, as can be seen in FIG. 9 showing RACK1 expression in horse cutaneous malignant melanoma, confirming the results already obtained in pigs and humans.

These data have been obtained using essentially the same protocol as described for analysis of human samples.

General Character of RACK1 Overexpression in Cutaneous Melanoma.

It is well known that all melanoma do not display the same set of primary clonal events, but some of them occur more frequently. In a recent review regarding the knowledge about primary clonal events, Bennett (39) reports the commonest affected genes in human cutaneous melanoma (see table 1 of this publication). As can be deduced from these data, no gene is affected in all cutaneous melanoma, suggesting that the mechanisms underlying the primary tumors derived from melanocytes, are heterogenous. For example, the CDKN2A gene is clonally altered in 78% of cutaneous melanoma; the B-RAF gene in 47% of cutaneous melanoma.

On the contrary, the present inventors have detected overexpression of RACK1 in all the samples from cutaneous and uveal melanoma that they have examined. This suggests that RACK1 may be a universal marker for melanoma, irrespective of the mechanism triggering the primary tumors in melanocytes.

This systematic overexpression of RACK1 in genetically heterogeneous tumors, may be explained by the positive regulation of RACK1, as a further step of tumoral progression of any melanoma.

RACK1 thus appears as the sole marker to be overexpressed in any melanocytes of cutaneous and uveal melanoma, which is very useful in the melanoma diagnostic for humans and other mammals.

Discussion

Few experimental animal models exist for cutaneous malignant melanomas. The murine models require a combination of gain of function and loss of function mutations in a protooncogene and tumor suppressor gene, respectively (1). Severe sunburn in newborn mice may be needed to induce skin melanomas with high penetrance (18). By contrast, the MeLiM swine model exhibits spontaneously cutaneous melanomas with histopathological features similar to human melanomas (6). Here, the inventors provide evidence that the hereditary disorder in MeLiM is useful for identifying regulatory complexes involved in the development of melanomas in pigs and humans. Indeed, they found that the intracellular receptor RACK1 is overexpressed in pig melanoma and also in human melanoma. This is the first time that a MeLiM model prediction is corroborated in human melanoma; it indicates that similar mechanisms are operating in the malignant transformation of melanocytes in pigs and man.

In the SAGE analysis, the RACK1 tag was more abundant in the library established from primary culture of metastatic melanoma cells than in the library from normal skin melanocytes. Consistently, RACK1 mRNA and protein were barely detected in normal epidermal melanocytes, but they were found at high levels in tumoral cells of cutaneous and metastatic melanoma. This holds true for every pig (n=38) and human (n=20) sample examined to date.

RACK1 contains seven internal Trp-Asp 40 (WD40) repeats which confer either stable or reversible binding capability to other proteins (19). Almost 60 proteins interacting with RACK1 have been described to date (Human Protein Reference Database) and RACK1 was shown to bind these partners in various cell compartments (19). Hence, RACK1 is believed to play a central role in cellular adaptation processes.

RACK1 has been identified first as a targeting protein for activated PKCβll (14). On the one hand, PKCβ is expressed in human cultured melanocytes (20). It has been further shown that when PKCβ and RACK1 are complexed and anchored on melanosomes, PKCβ phosphorylates tyrosinase, the key enzyme of melanogenesis (21) suggesting that, in normal melanocytes, PKCβ acts mainly by stimulating melanogenesis. On the other hand, indirect observations argue for a possible role of PKCβll in melanoma development. First, PKCβll has been shown to directly phosphorylate AKT in mast cells (22), and AKT is known to promote cell survival and development of malignant melanoma (23). Second, WNT 5A has been identified as a robust marker of the highly invasive behaviour of human melanoma cells and WNT5a is believed to mediate this effect by its ability to activate PKC (3). Based on these observations, the inventors analysed PKCβll expression in pig and human melanomas. PKCβll was hardly detected in normal skin melanocytes and was not up-regulated in malignant melanocytes compared to normal skin melanocytes. Moreover, PKCβ expression is lost in 90% of melanoma cell lines (24). Altogether, it is unlikely that the effects of overexpression of RACK1 in tumoral melanocytes depend on PKCβll. However RACK1 could interact with other PKC isoforms.

The inventors detected RACK1 in the nucleus of 15% of pig metastatic melanoma cells. Nuclear translocation of RACK1 has already been observed. Briefly, following acute exposure of rodents to alcohol, RACK1 is uncoupled from PKCβll and translocated to the nucleus of hippocampal neurons (25). In the nucleus, RACK1 mediates the induction of several genes including BDNF (26). BDNF increase leads to enhanced expression of dopamine D3 receptor, which negatively regulates ethanol intake (27). Since it has been reported that melanoma metastases more frequently express BDNF and its receptor than primary cutaneous malignant melanomas (28), the inventors tested whether BDNF would be expressed in MeLiM metastases. However, no BDNF expression was detected in melanoma cells of MeLiM metastases, thus suggesting that nuclear RACK1 mediates a BDNF independent cellular response in melanocytes.

Few studies have detected up-regulation of RACK1 in vivo in human cancers (13, 29) and none of them in connection withk melanocytes. RACK1 mRNA was found to be strongly expressed in five non-small cell lung carcinomas; the endothelium of large vessels was identified as a major site for RACK1 expression in these tumors (13). RACK1 mRNA was also highly expressed in 11 cases of colorectal cancer, with a stronger expression in cancer cells than in non-cancer regions (29). There was however no disclosure of overexpression of RACK-1 in tumoral melanocyte cells.

Here, the inventors show that RACK1 mRNA and its corresponding protein are systematically overexpressed in cutaneous and metastatic melanomas; RACK1 level was elevated in the transformed melanocytes themselves.

The proposal that RACK1 overexpression might be instrumental in the progression of malignant cutaneous melanomas is supported by some experiments, which were however performed on cultured cell lines. Indeed, increasing and decreasing RACK1 levels revealed multiple cellular functions related to cell transformation. Overexpression of RACK1 has been shown to inhibit the growth of 3T3 fibroblasts (30, 31). However, blockade of RACK1 translation with morpholino oligonucleotides also reduced 3T3 fibroblast growth (31), altogether suggesting that RACK1 protein level is actively regulated in cultured cells. Interestingly, overexpression of RACK1 enhanced the proliferation rate of MCF-7 breast carcinoma cells, indicating differential effects of RACK1 in fibroblasts and tumoral cells (32). Furthermore, RACK1 inhibited apoptosis induced by serum starvation in PC-12 pheochromocytoma cells (33), or by several apoptotic stimuli in W7.2 T cells (34).

More specifically, MeWo human melanoma cells overexpressing RACK1 were found to exhibit increased resistance to UV-induced apoptosis (35). This effect is mediated by RACK1 as an adaptor protein to facilitate the activation of JNK by PKC (35). In addition, RACK1 overexpression in normally non-motile MCF7 carcinoma cells was reported to increase their migratory capacity in wound healing assays and to induce their motility in Transwell assays. Accordingly, suppression of RACK1 expression using siRNA had opposite effects in prostate carcinoma DU145 cells, inhibiting their migration in Transwell assays (36).

The promotion of cell migration by RACK1 upregulation was recently proposed to rely on its association with IGF-1R and either the protein phosphatase 2a (PP2A) or β1 integrin. Indeed, in cells overexpressing RACK1, RACK1 releases PP2A and associates with β1 integrin thus enhancing integrin signalling and conferring increased cell migration capacity.

Overexpression of RACK1 was also able to enhance the insulin- and IGF-1-promoted anchorage-independent growth of several human ovarian cancer cell lines (37). Again, this effect is mediated through RACK1 acting as an adaptor protein, in this context for insulin receptor (IR)/IGF-1R and STAT3 (37).

Interestingly, the overexpression of RACK1 in MeWo melanocytes has been shown to enhance insulin-induced activation of STAT3, implying that the components of the pathway are present in these melanoma-derived cells (37). Finally, inhibition of RACK1 expression in MeWo melanoma cells using siRNA for RACK1 reduced significantly tumor growth in nude mice after subcutaneous injection (35).

Each of these observations supports the view that RACK1 overexpression is a causal event in the progression of malignant cutaneous melanoma in MeLiM swine model and human patients.

In conclusion, RACK1 appears as a point of convergence of several signalling pathways involved in cell proliferation, resistance to apoptosis, migratory and spreading abilities, and its deregulation is likely to lead to tumoral transformation in the melanocyte lineage.

References

1. Chin L. The genetics of malignant melanoma: lessons from mouse and man. Nat Rev Cancer 2003; 3:559-70.

2. Clark E A, Golub TR1 Lander E S, Hynes R O. Genomic analysis of metastasis reveals an essential role for RhoC. Nature 2000; 406:532-5.

3. Weeraratna A T, Jiang Y, Hostetter G, et al. Wnt5a signaling directly affects cell motility and invasion of metastatic melanoma. Cancer Cell 2002; 1:279-88.

4. Hoek K, Rimm D L, Williams K R, et al. Expression profiling reveals novel pathways in the transformation of melanocytes to melanomas. Cancer Res 2004; 64:5270-82.

5. Weeraratna A T, Becker D, Can K M, et al. Generation and analysis of melanoma SAGE libraries: SAGE advice on the melanoma transcriptome. Oncogene 2004; 23:2264-74.

6. Vincent-Naulleau S, Le Chalony C, Leplat J J, et al. Clinical and histopathological characterization of cutaneous melanomas in the melanoblastoma-bearing Libechov minipig model. Pigment Cell Res 2004; 17:24-35.

7. Velculescu V E, Zhang L, Vogelstein B, Kinzler K W. Serial analysis of gene expression. Science 1995; 270:484-7.

8. Jule S, Bosse P, Egidy G, Panthier J J. Establishment and characterization of a normal melanocyte cell line derived from pig skin. Pigment Cell Res 2003; 16:407-10.

9. Le Chalony C, Renard C, Vincent-Naulleau S, et al. CDKN2A region polymorphism and genetic susceptibility to melanoma in the melim swine model of familial melanoma, Int J Cancer 2003; 103:631-5.

10. Virion B, Cheval L, Buhler J M, et al. Serial microanalysis of renal transcriptomes. Proc Natl Acad Sci USA 1999; 96:15286-91.

11. Egidy G, Juillerat-Jeanneret L, Jeannin J F, et al. Modulation of human colon tumorstromal interactions by the endothelin system. Am J Pathol 2000; 157: 1863-74.

12. Johren O, Sanvitto G L, Egidy G, Saavedra J M. Angiotensin Il AT1A receptor mRNA expression is induced by estrogen-progesterone in dopaminergic neurons of the female rat arcuate nucleus. J Neurosci 1997; 17:8283-92.

13. Berns H, Humar R, Hengerer B, Kiefer F N, Battegay E J. RACK1 is up-regulated in angiogenesis and human carcinomas. Faseb J 2000; 14:2549-58.

14. Ron D, Jiang Z, Yao L, et al. Coordinated movement of RACK1 with activated betaIIPKC. J Biol Chem 1999; 274: 27039-46.

15. Rubinfeld B, Robbins P, El-Gamil M, et al. Stabilization of beta-catenin by genetic defects in melanoma cell lines. Science 1997; 275: 1790-2.

16. Wullschleger S, Loewith R, Hall M N. TOR signaling in growth and metabolism. Cell 2006; 124:471-84.

17. King R, Weilbaecher K N, McGill G, et al. Microphthalmia transcription factor. A sensitive and specific melanocyte marker for Melanoma Diagnosis. Am J Pathol 1999; 155:731-8.

19. McCahill A, Warwicker J, Bolger G B, Houslay M D, Yarwood S J. The RACK1 scaffold protein: a dynamic cog in cell response mechanisms. Mol Pharmacol 2002; 62:1261-73.

20. Oka M, Ogita K, Ando H, Kikkawa U, Ichihashi M. Differential down-regulation of protein kinase C subspecies in normal human melanocytes: possible involvement of the zeta subspecies in growth regulation. J Invest Dermatol 1995; 105:567-71.

21. Park H Y, Wu H, Killoran C E, Gilchrest B A. The receptor for activated C-kinase-1 (RACK-I) anchors activated PKC-beta on melanosomes. J Cell Sci 2004; 117:3659-68.

22. Kawakami Y, Nishimoto H, Kitaura J, et al. Protein kinase C betaII regulates Akt phosphorylation on Ser-473 in a cell type- and stimulus-specific fashion. J Biol Chem 2004; 279:47720-5.

23. Stahl J M, Sharma A, Cheung M, et al. Deregulated Akt3 activity promotes development of malignant melanoma. Cancer Res 2004; 64:7002-10.

24. Gilhooly E M, Morse-Gaudio M, Bianchi L, et al. Loss of expression of protein kinase C beta is a common phenomenon in human malignant melanoma: a result of transformation or differentiation? Melanoma Res 2001; 11:355-69.

25. Ron D, Vagts A J, Dohrman D P, et al. Uncoupling of betaIIPKC from its targeting protein RACK1 in response to ethanol in cultured cells and mouse brain. Faseb J 2000; 14:2303-14.

26. McGough N N, He D Y, Logrip M L, et al. RACK1 and brain-derived neurotrophic factor: a homeostatic pathway that regulates alcohol addiction. J Neurosci 2004; 24: 10542-52.

27. Jeanblanc J, He D Y, McGough N N, et al. The dopamine D3 receptor is part of a homeostatic pathway regulating ethanol consumption. J Neurosci 2006; 26:1457-64.

28. Innominato P F, Libbrecht L, van den Oord J J. Expression of neurotrophins and their receptors in pigment cell lesions of the skin. J Pathol 2001; 194:95-100.

29. Saito A, Fujii G, Sato Y, et al. Detection of genes expressed in primary colon cancers by in situ hybridisation: overexpression of RACK 1. Mol Pathol 2002; 55:34-9.

30. Chang B Y, Conroy K B, Machleder E M, Cartwright C A. RACK1, a receptor for activated C kinase and a homolog of the beta subunit of G proteins, inhibits activity of src tyrosine kinases and growth of NIH 3T3 cells. Mol Cell Biol 1998; 18:3245-56.

31. Hermanto U, Zong C S, Li W, Wang L H. RACK1, an insulin-like growth factor I (IGF-I) receptor-interacting protein, modulates IGF-1-dependent integrin signaling and promotes cell spreading and contact with extracellular matrix. Mol Cell Biol 2002; 22:2345-65.

32. Kiely P A, Sant A, O'Connor R. RACK1 is an insulin-like growth factor 1 (IGF-1) receptor-interacting protein that can regulate IGF-1-mediated Akt activation and protection from cell death. J Biol Chem 2002; 277:22581-9.

33. Choi D S, Young H, McMahon T, Wang D, Messing R O. The mouse RACK1 gene is regulated by nuclear factor-kappa B and contributes to cell survival. Mol Pharmacol 2003; 64:1541-8.

34. Mourtada-Maarabouni M, Kirkham L, Farzaneh F, Williams G T. Functional expression cloning reveals a central role for the receptor for activated protein kinase C 1 (RACK1) in T cell apoptosis. J Leukoc Biol 2005; 78:503-14.

35. Lopez-Bergami P, Habelhah H, Bhoumik A, et al. RACK1 mediates activation of JNK by protein kinase C [corrected]. Mol Cell 2005; 19:309-20.

36. Kiely P A, O'Gorman D, Luong K, Ron D, O'Connor R. Insulin-like growth factor I controls a mutually exclusive association of RACK1 with protein phosphatase 2A and betaI integrin to promote cell migration. Mol Cell Biol 2006; 26:4041-51.

37. Zhang W, Zong C S, Hermanto U, et al. RACK1 Recruits STAT3 Specifically to Insulin and Insulin-Like Growth Factor 1 Receptors for Activation, Which Is Important for Regulating Anchorage-Independent Growth. Mol Cell Biol 2006; 26:413-24.

38. White V A, et al. Correlation of cytogenetic abnormalities with the outcome of patients with uveal melanoma. Cancer 1998; 83(2):354-9.

39. Bennett D. C. How to make a melanoma: what do we know of the primary clonal events? Pigment Cell Melanoma Res. 2008; 21: 27-38.

The invention claimed is:

1. A method for detecting the level of expression of RACK-1 mRNA comprising:
   a) providing a biopsy comprising melanocytes from a human patient; and
   b) performing an in situ hybridization assay on the biopsy to detect the level of expression of RACK-1 mRNA in the melanocytes.

2. The method of claim 1, wherein high expression of RACK-1 mRNA is detected in the melanocytes.

3. The method of claim 1, wherein low expression of RACK-1 mRNA is detected in the melanocytes.

4. The method of claim 1, wherein the melanocytes are epidermal melanocytes.

5. The method of claim 1, wherein the biopsy is a skin biopsy.

6. The method of claim 1, wherein the biopsy is an eye biopsy.

7. The method of claim 1, further comprising performing an in situ immunoassay on the biopsy to detect melanocytes in the biopsy with an antibody.

8. The method of claim 7, wherein the antibody for detecting melanocytes is a monoclonal antibody.

9. The method of claim 7, wherein the antibody for detecting melanocytes is against the microphthalmia transcription factor MITF, the dopachrome tautomerase DCT, the tyrosinase TYR, or the tyrosinase-related protein 1 TRP1.

10. A method for detecting the level of expression of RACK-1 mRNA comprising:
    a) providing a biopsy comprising melanocytes from a horse or dog; and
    b) performing an in situ hybridization assay on the biopsy to detect the level of expression of RACK-1 mRNA in the melanocytes.

11. The method of claim 10, wherein the melanocytes are epidermal melanocytes.

12. The method of claim 10, wherein the biopsy is a skin biopsy.

13. The method of claim 10, wherein the biopsy is an eye biopsy.

14. The method of claim 10, further comprising performing an in situ immunoassay on the biopsy to detect melanocytes in the biopsy with an antibody.

15. The method of claim 14, wherein the antibody for detecting melanocytes is a monoclonal antibody.

16. The method of claim 14, wherein the antibody for detecting melanocytes is against the microphthalmia transcription factor MITF, the dopachrome tautomerase DCT, the tyrosinase TYR, or the tyrosinase-related protein 1 TRP1.

17. The method of claim 10, wherein a biopsy comprising melanocytes from a horse is provided.

18. The method of claim 10, wherein a biopsy comprising melanocytes from a dog is provided.

\* \* \* \* \*

SEQUENCE LISTING

```
<160> NUMBER OF SEQ ID NOS: 69

<210> SEQ ID NO 1
<211> LENGTH: 10
<212> TYPE: DNA
<213> ORGANISM: Artificial
<220> FEATURE:
<223> OTHER INFORMATION: Tag sequence

<400> SEQUENCE: 1
attgtagatg                                                           10

<210> SEQ ID NO 2
<211> LENGTH: 10
<212> TYPE: DNA
<213> ORGANISM: Artificial
<220> FEATURE:
<223> OTHER INFORMATION: tag

<400> SEQUENCE: 2
acatccatca                                                           10

<210> SEQ ID NO 3
<211> LENGTH: 10
<212> TYPE: DNA
<213> ORGANISM: Artificial
<220> FEATURE:
<223> OTHER INFORMATION: tag
```

```
<400> SEQUENCE: 3
aaaccaaaga                                                            10

<210> SEQ ID NO 4
<211> LENGTH: 10
<212> TYPE: DNA
<213> ORGANISM: Artificial
<220> FEATURE:
<223> OTHER INFORMATION: tag

<400> SEQUENCE: 4
tgactataac                                                            10

<210> SEQ ID NO 5
<211> LENGTH: 10
<212> TYPE: DNA
<213> ORGANISM: Artificial
<220> FEATURE:
<223> OTHER INFORMATION: tag

<400> SEQUENCE: 5
aagttcccgc                                                            10

<210> SEQ ID NO 6
<211> LENGTH: 10
<212> TYPE: DNA
<213> ORGANISM: Artificial
<220> FEATURE:
<223> OTHER INFORMATION: tag

<400> SEQUENCE: 6
aacctaatta                                                            10

<210> SEQ ID NO 7
<211> LENGTH: 10
<212> TYPE: DNA
<213> ORGANISM: Artificial
<220> FEATURE:
<223> OTHER INFORMATION: tag

<400> SEQUENCE: 7
aactcaataa                                                            10

<210> SEQ ID NO 8
<211> LENGTH: 10
<212> TYPE: DNA
<213> ORGANISM: Artificial
<220> FEATURE:
<223> OTHER INFORMATION: tag

<400> SEQUENCE: 8
aaagattaag                                                            10

<210> SEQ ID NO 9
<211> LENGTH: 10
<212> TYPE: DNA
<213> ORGANISM: Artificial
<220> FEATURE:
<223> OTHER INFORMATION: tag

<400> SEQUENCE: 9
agttatgaag                                                            10
```

```
<210> SEQ ID NO 10
<211> LENGTH: 10
<212> TYPE: DNA
<213> ORGANISM: Artificial
<220> FEATURE:
<223> OTHER INFORMATION: tag

<400> SEQUENCE: 10
aagctacaca                                                          10

<210> SEQ ID NO 11
<211> LENGTH: 10
<212> TYPE: DNA
<213> ORGANISM: Artificial
<220> FEATURE:
<223> OTHER INFORMATION: tag

<400> SEQUENCE: 11
cagagggaca                                                          10

<210> SEQ ID NO 12
<211> LENGTH: 10
<212> TYPE: DNA
<213> ORGANISM: Artificial
<220> FEATURE:
<223> OTHER INFORMATION: tag

<400> SEQUENCE: 12
acaactgggg                                                          10

<210> SEQ ID NO 13
<211> LENGTH: 10
<212> TYPE: DNA
<213> ORGANISM: Artificial
<220> FEATURE:
<223> OTHER INFORMATION: tag

<400> SEQUENCE: 13
tgatagaaga                                                          10

<210> SEQ ID NO 14
<211> LENGTH: 10
<212> TYPE: DNA
<213> ORGANISM: Artificial
<220> FEATURE:
<223> OTHER INFORMATION: tag

<400> SEQUENCE: 14
tatgaataag                                                          10

<210> SEQ ID NO 15
<211> LENGTH: 10
<212> TYPE: DNA
<213> ORGANISM: Artificial
<220> FEATURE:
<223> OTHER INFORMATION: tag

<400> SEQUENCE: 15
agtatcaaca                                                          10

<210> SEQ ID NO 16
<211> LENGTH: 10
<212> TYPE: DNA
<213> ORGANISM: Artificial
<220> FEATURE:
<223> OTHER INFORMATION: tag
```

```
<400> SEQUENCE: 16
tgctcaggct                                                          10

<210> SEQ ID NO 17
<211> LENGTH: 10
<212> TYPE: DNA
<213> ORGANISM: Artificial
<220> FEATURE:
<223> OTHER INFORMATION: tag

<400> SEQUENCE: 17
aatacaagtt                                                          10

<210> SEQ ID NO 18
<211> LENGTH: 10
<212> TYPE: DNA
<213> ORGANISM: Artificial
<220> FEATURE:
<223> OTHER INFORMATION: tag

<400> SEQUENCE: 18
gaggtggaga                                                          10

<210> SEQ ID NO 19
<211> LENGTH: 10
<212> TYPE: DNA
<213> ORGANISM: Artificial
<220> FEATURE:
<223> OTHER INFORMATION: tag

<400> SEQUENCE: 19
atttctaggc                                                          10

<210> SEQ ID NO 20
<211> LENGTH: 10
<212> TYPE: DNA
<213> ORGANISM: Artificial
<220> FEATURE:
<223> OTHER INFORMATION: tag

<400> SEQUENCE: 20
tcacccgcaa                                                          10

<210> SEQ ID NO 21
<211> LENGTH: 10
<212> TYPE: DNA
<213> ORGANISM: Artificial
<220> FEATURE:
<223> OTHER INFORMATION: tag

<400> SEQUENCE: 21
tcgtccctgt                                                          10

<210> SEQ ID NO 22
<211> LENGTH: 10
<212> TYPE: DNA
<213> ORGANISM: Artificial
<220> FEATURE:
<223> OTHER INFORMATION: tag

<400> SEQUENCE: 22
cctgtgctga                                                          10
```

```
<210> SEQ ID NO 23
<211> LENGTH: 10
<212> TYPE: DNA
<213> ORGANISM: Artificial
<220> FEATURE:
<223> OTHER INFORMATION: tag

<400> SEQUENCE: 23
ggtcattcat                                                          10

<210> SEQ ID NO 24
<211> LENGTH: 10
<212> TYPE: DNA
<213> ORGANISM: Artificial
<220> FEATURE:
<223> OTHER INFORMATION: tag

<400> SEQUENCE: 24
tcgcctggac                                                          10

<210> SEQ ID NO 25
<211> LENGTH: 10
<212> TYPE: DNA
<213> ORGANISM: Artificial
<220> FEATURE:
<223> OTHER INFORMATION: tag

<400> SEQUENCE: 25
tcgtcccttc                                                          10

<210> SEQ ID NO 26
<211> LENGTH: 10
<212> TYPE: DNA
<213> ORGANISM: Artificial
<220> FEATURE:
<223> OTHER INFORMATION: tag

<400> SEQUENCE: 26
attcatgtca                                                          10

<210> SEQ ID NO 27
<211> LENGTH: 10
<212> TYPE: DNA
<213> ORGANISM: Artificial
<220> FEATURE:
<223> OTHER INFORMATION: tag

<400> SEQUENCE: 27
gtctaatcac                                                          10

<210> SEQ ID NO 28
<211> LENGTH: 10
<212> TYPE: DNA
<213> ORGANISM: Artificial
<220> FEATURE:
<223> OTHER INFORMATION: tag

<400> SEQUENCE: 28
aatgaccgac                                                          10

<210> SEQ ID NO 29
<211> LENGTH: 10
<212> TYPE: DNA
<213> ORGANISM: Artificial
<220> FEATURE:
<223> OTHER INFORMATION: tag
```

```
<400> SEQUENCE: 29
cacccgcaat                                                                10

<210> SEQ ID NO 30
<211> LENGTH: 10
<212> TYPE: DNA
<213> ORGANISM: Artificial
<220> FEATURE:
<223> OTHER INFORMATION: tag

<400> SEQUENCE: 30
ccttccgact                                                                10

<210> SEQ ID NO 31
<211> LENGTH: 10
<212> TYPE: DNA
<213> ORGANISM: Artificial
<220> FEATURE:
<223> OTHER INFORMATION: tag

<400> SEQUENCE: 31
cgtccctgtg                                                                10

<210> SEQ ID NO 32
<211> LENGTH: 10
<212> TYPE: DNA
<213> ORGANISM: Artificial
<220> FEATURE:
<223> OTHER INFORMATION: tag

<400> SEQUENCE: 32
agataatttg                                                                10

<210> SEQ ID NO 33
<211> LENGTH: 10
<212> TYPE: DNA
<213> ORGANISM: Artificial
<220> FEATURE:
<223> OTHER INFORMATION: tag

<400> SEQUENCE: 33
atagacgagc                                                                10

<210> SEQ ID NO 34
<211> LENGTH: 10
<212> TYPE: DNA
<213> ORGANISM: Artificial
<220> FEATURE:
<223> OTHER INFORMATION: tag

<400> SEQUENCE: 34
ctgcattgct                                                                10

<210> SEQ ID NO 35
<211> LENGTH: 10
<212> TYPE: DNA
<213> ORGANISM: Artificial
<220> FEATURE:
<223> OTHER INFORMATION: tag

<400> SEQUENCE: 35
agaatataag                                                                10
```

```
<210> SEQ ID NO 36
<211> LENGTH: 10
<212> TYPE: DNA
<213> ORGANISM: Artificial
<220> FEATURE:
<223> OTHER INFORMATION: tag

<400> SEQUENCE: 36
ccgcgttgct                                                            10

<210> SEQ ID NO 37
<211> LENGTH: 10
<212> TYPE: DNA
<213> ORGANISM: Artificial
<220> FEATURE:
<223> OTHER INFORMATION: tag

<400> SEQUENCE: 37
atgaagatat                                                            10

<210> SEQ ID NO 38
<211> LENGTH: 10
<212> TYPE: DNA
<213> ORGANISM: Artificial
<220> FEATURE:
<223> OTHER INFORMATION: tag

<400> SEQUENCE: 38
tgctgcaggg                                                            10

<210> SEQ ID NO 39
<211> LENGTH: 10
<212> TYPE: DNA
<213> ORGANISM: Artificial
<220> FEATURE:
<223> OTHER INFORMATION: tag

<400> SEQUENCE: 39
gtcgttctgg                                                            10

<210> SEQ ID NO 40
<211> LENGTH: 10
<212> TYPE: DNA
<213> ORGANISM: Artificial
<220> FEATURE:
<223> OTHER INFORMATION: tag

<400> SEQUENCE: 40
agactttaa                                                             10

<210> SEQ ID NO 41
<211> LENGTH: 10
<212> TYPE: DNA
<213> ORGANISM: Artificial
<220> FEATURE:
<223> OTHER INFORMATION: tag

<400> SEQUENCE: 41
gactttgaca                                                            10

<210> SEQ ID NO 42
<211> LENGTH: 10
<212> TYPE: DNA
<213> ORGANISM: Artificial
<220> FEATURE:
<223> OTHER INFORMATION: tag
```

```
<400> SEQUENCE: 42
tctggaaaga                                                          10

<210> SEQ ID NO 43
<211> LENGTH: 10
<212> TYPE: DNA
<213> ORGANISM: Artificial
<220> FEATURE:
<223> OTHER INFORMATION: tag

<400> SEQUENCE: 43
tctgactacc                                                          10

<210> SEQ ID NO 44
<211> LENGTH: 10
<212> TYPE: DNA
<213> ORGANISM: Artificial
<220> FEATURE:
<223> OTHER INFORMATION: tag

<400> SEQUENCE: 44
agaaagctgt                                                          10

<210> SEQ ID NO 45
<211> LENGTH: 10
<212> TYPE: DNA
<213> ORGANISM: Artificial
<220> FEATURE:
<223> OTHER INFORMATION: tag

<400> SEQUENCE: 45
agcgttcagc                                                          10

<210> SEQ ID NO 46
<211> LENGTH: 10
<212> TYPE: DNA
<213> ORGANISM: Artificial
<220> FEATURE:
<223> OTHER INFORMATION: tag

<400> SEQUENCE: 46
aggggaaatg                                                          10

<210> SEQ ID NO 47
<211> LENGTH: 10
<212> TYPE: DNA
<213> ORGANISM: Artificial
<220> FEATURE:
<223> OTHER INFORMATION: tag

<400> SEQUENCE: 47
accctggctg                                                          10

<210> SEQ ID NO 48
<211> LENGTH: 10
<212> TYPE: DNA
<213> ORGANISM: Artificial
<220> FEATURE:
<223> OTHER INFORMATION: tag

<400> SEQUENCE: 48
ctaaaaaaaa                                                          10
```

```
<210> SEQ ID NO 49
<211> LENGTH: 10
<212> TYPE: DNA
<213> ORGANISM: Artificial
<220> FEATURE:
<223> OTHER INFORMATION: tag

<400> SEQUENCE: 49
tcagaagaga                                                          10

<210> SEQ ID NO 50
<211> LENGTH: 10
<212> TYPE: DNA
<213> ORGANISM: Artificial
<220> FEATURE:
<223> OTHER INFORMATION: tag

<400> SEQUENCE: 50
tcacctgggg                                                          10

<210> SEQ ID NO 51
<211> LENGTH: 10
<212> TYPE: DNA
<213> ORGANISM: Artificial
<220> FEATURE:
<223> OTHER INFORMATION: tag

<400> SEQUENCE: 51
cccaacaatg                                                          10

<210> SEQ ID NO 52
<211> LENGTH: 10
<212> TYPE: DNA
<213> ORGANISM: Artificial
<220> FEATURE:
<223> OTHER INFORMATION: tag

<400> SEQUENCE: 52
tctaaagcgg                                                          10

<210> SEQ ID NO 53
<211> LENGTH: 10
<212> TYPE: DNA
<213> ORGANISM: Artificial
<220> FEATURE:
<223> OTHER INFORMATION: tag

<400> SEQUENCE: 53
agtggctttg                                                          10

<210> SEQ ID NO 54
<211> LENGTH: 10
<212> TYPE: DNA
<213> ORGANISM: Artificial
<220> FEATURE:
<223> OTHER INFORMATION: tag

<400> SEQUENCE: 54
agcatccaga                                                          10

<210> SEQ ID NO 55
<211> LENGTH: 10
<212> TYPE: DNA
<213> ORGANISM: Artificial
<220> FEATURE:
<223> OTHER INFORMATION: tag
```

```
<400> SEQUENCE: 55
cagagctgcc                                                          10

<210> SEQ ID NO 56
<211> LENGTH: 10
<212> TYPE: DNA
<213> ORGANISM: Artificial
<220> FEATURE:
<223> OTHER INFORMATION: tag

<400> SEQUENCE: 56
ctagacgact                                                          10

<210> SEQ ID NO 57
<211> LENGTH: 10
<212> TYPE: DNA
<213> ORGANISM: Artificial
<220> FEATURE:
<223> OTHER INFORMATION: tag

<400> SEQUENCE: 57
agatggccag                                                          10

<210> SEQ ID NO 58
<211> LENGTH: 10
<212> TYPE: DNA
<213> ORGANISM: Artificial
<220> FEATURE:
<223> OTHER INFORMATION: tag

<400> SEQUENCE: 58
agcttaagca                                                          10

<210> SEQ ID NO 59
<211> LENGTH: 10
<212> TYPE: DNA
<213> ORGANISM: Artificial
<220> FEATURE:
<223> OTHER INFORMATION: tag

<400> SEQUENCE: 59
atgtgcctgg                                                          10

<210> SEQ ID NO 60
<211> LENGTH: 10
<212> TYPE: DNA
<213> ORGANISM: Artificial
<220> FEATURE:
<223> OTHER INFORMATION: tag

<400> SEQUENCE: 60
tatgggggtc                                                          10

<210> SEQ ID NO 61
<211> LENGTH: 10
<212> TYPE: DNA
<213> ORGANISM: Artificial
<220> FEATURE:
<223> OTHER INFORMATION: tag

<400> SEQUENCE: 61
tgtcaaaaaa                                                          10
```

```
<210> SEQ ID NO 62
<211> LENGTH: 10
<212> TYPE: DNA
<213> ORGANISM: Artificial
<220> FEATURE:
<223> OTHER INFORMATION: tag

<400> SEQUENCE: 62
agcctggacc                                                             10

<210> SEQ ID NO 63
<211> LENGTH: 10
<212> TYPE: DNA
<213> ORGANISM: Artificial
<220> FEATURE:
<223> OTHER INFORMATION: tag

<400> SEQUENCE: 63
agggaatgga                                                             10

<210> SEQ ID NO 64
<211> LENGTH: 10
<212> TYPE: DNA
<213> ORGANISM: Artificial
<220> FEATURE:
<223> OTHER INFORMATION: tag

<400> SEQUENCE: 64
cctagcctgg                                                             10

<210> SEQ ID NO 65
<211> LENGTH: 10
<212> TYPE: DNA
<213> ORGANISM: Artificial
<220> FEATURE:
<223> OTHER INFORMATION: tag

<400> SEQUENCE: 65
tggcatggct                                                             10

<210> SEQ ID NO 66
<211> LENGTH: 10
<212> TYPE: DNA
<213> ORGANISM: Artificial
<220> FEATURE:
<223> OTHER INFORMATION: tag

<400> SEQUENCE: 66
cactgctcaa                                                             10

<210> SEQ ID NO 67
<211> LENGTH: 10
<212> TYPE: DNA
<213> ORGANISM: Artificial
<220> FEATURE:
<223> OTHER INFORMATION: tag

<400> SEQUENCE: 67
agctgttcta                                                             10

<210> SEQ ID NO 68
<211> LENGTH: 10
<212> TYPE: DNA
<213> ORGANISM: Artificial
<220> FEATURE:
<223> OTHER INFORMATION: tag
```

-continued

```
<400> SEQUENCE: 68
cacccgcaat                                                          10

<210> SEQ ID NO 69
<211> LENGTH: 317
<212> TYPE: PRT
<213> ORGANISM: Homo sapiens

<400> SEQUENCE: 69

Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
        35                  40                  45

Glu Thr Asn Tyr Gly Ile Pro Gln Arg Ala Leu Arg Gly His Ser His
    50                  55                  60

Phe Val Ser Asp Val Val Ile Ser Ser Asp Gly Gln Phe Ala Leu Ser
65                  70                  75                  80

Gly Ser Trp Asp Gly Thr Leu Arg Leu Trp Asp Leu Thr Thr Gly Thr
                85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
    130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
    210                 215                 220

Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
                245                 250                 255

Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Pro Gln Cys Thr Ser
        275                 280                 285

Leu Ala Trp Ser Ala Asp Gly Gln Thr Leu Phe Ala Gly Tyr Thr Asp
    290                 295                 300

Asn Leu Val Arg Val Trp Gln Val Thr Ile Gly Thr Arg
305                 310                 315
```